US008475536B2

(12) United States Patent  
Tong et al.

(10) Patent No.: US 8,475,536 B2  
(45) Date of Patent: Jul. 2, 2013

(54) METHODS AND DEVICES FOR IMPLANTS WITH IMPROVED CEMENT ADHESION

(75) Inventors: Weidong Tong, Warsaw, IN (US); Steve Leisinger, Columbia City, IN (US); Lawrence Salvati, Goshen, IN (US); John Bonitati, Warsaw, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 12/696,880

(22) Filed: Jan. 29, 2010

(65) Prior Publication Data

US 2011/0190902 A1   Aug. 4, 2011

(51) Int. Cl.
*A61F 2/28* (2006.01)
(52) U.S. Cl.
USPC ........................................ 623/23.57
(58) Field of Classification Search
USPC ................. 623/23.55–23.57; 427/2.24–2.27
See application file for complete search history.

(56) References Cited

U.S. PATENT DOCUMENTS

| | | | |
|---|---|---|---|
| 3,848,272 A | 11/1974 | Noiles | |
| 3,855,638 A | 12/1974 | Pilliar | |
| 4,145,764 A | 3/1979 | Suzuki et al. | |
| 4,156,943 A | 6/1979 | Collier | |
| 4,206,516 A | 6/1980 | Pilliar | |
| 4,309,488 A | 1/1982 | Heide et al. | |
| 4,330,891 A | 5/1982 | Branemark et al. | |
| 4,476,590 A | 10/1984 | Scales et al. | |
| 4,483,678 A | 11/1984 | Nishio et al. | |
| 4,612,160 A | 9/1986 | Donlevy et al. | |
| 4,678,523 A | 7/1987 | Sridhar et al. | |
| 4,713,076 A | 12/1987 | Draenert | |
| 4,746,532 A | 5/1988 | Suzuki et al. | |
| 4,780,450 A | 10/1988 | Sauk et al. | |
| 4,846,837 A | 7/1989 | Kurse et al. | |
| 4,955,911 A | 9/1990 | Frey et al. | |

(Continued)

FOREIGN PATENT DOCUMENTS

| | | |
|---|---|---|
| CA | 2108362 | 10/1992 |
| DE | 3409372 A1 | 9/1985 |

(Continued)

OTHER PUBLICATIONS

Anissian, H. et al., "Metal-on-Metal Bearing in hip Prosthesis Generates 100-fold Less Wear Debris than Metal-on-Polyethylene," Acta Orthopadica Scandanavica 70(6):578-82 (1999).

(Continued)

*Primary Examiner* — David Isabella
*Assistant Examiner* — Ann Schillinger

(57) ABSTRACT

Biomedical implants (e.g., orthopedic implants) with modified surfaces that can enhance a cement bond's strength (e.g., tensile, shear, and/or fatigue) are disclosed, along with methods of manufacturing and using such implants. The implants can exhibit a variety of physical, chemical, or process-derived features which can enhance cement bonding. For instance, the implant surface can exhibit particular roughness values, and/or be substantially free of non native material. Processes for producing such implants can include providing a first roughened implant surface, which can be produced, for example, by particle blasting. A treatment formulation can be applied to the first roughened surface to create a second roughened surface that exhibits enhanced cement bonding properties relative to the first roughened surface. In some instances, the first roughened surface and the second roughened surface can exhibit substantially similar $R_a$ values. The second roughened surface can exhibit a negative $R_{sk}$ value.

11 Claims, 15 Drawing Sheets

U.S. PATENT DOCUMENTS

| | | | |
|---|---|---|---|
| 4,990,163 | A | 2/1991 | Ducheyne et al. |
| 5,030,233 | A * | 7/1991 | Ducheyne .................. 623/23.54 |
| 5,068,122 | A | 11/1991 | Kokubo et al. |
| 5,084,051 | A | 1/1992 | Tormala et al. |
| 5,141,522 | A | 8/1992 | Landi |
| 5,157,111 | A | 10/1992 | Pachence |
| 5,171,273 | A | 12/1992 | Silver et al. |
| 5,180,393 | A | 1/1993 | Commarmond |
| 5,205,921 | A | 4/1993 | Shirkanzadeh |
| 5,222,987 | A | 6/1993 | Jones |
| 5,258,029 | A | 11/1993 | Chu et al. |
| 5,310,539 | A | 5/1994 | Williams |
| 5,368,881 | A | 11/1994 | Kelman et al. |
| 5,478,237 | A | 12/1995 | Ishizawa |
| 5,508,267 | A | 4/1996 | Czernuszka et al. |
| 5,543,441 | A | 8/1996 | Rhee et al. |
| 5,573,771 | A | 11/1996 | Geistlich et al. |
| 5,607,480 | A | 3/1997 | Beaty |
| 5,658,333 | A | 8/1997 | Kelman et al. |
| 5,681,310 | A | 10/1997 | Yuan et al. |
| 5,824,093 | A | 10/1998 | Ray et al. |
| 5,906,828 | A | 5/1999 | Cima et al. |
| 6,022,376 | A | 2/2000 | Assell et al. |
| 6,031,148 | A | 2/2000 | Hayes et al. |
| 6,066,175 | A | 5/2000 | Henderson et al. |
| 6,066,176 | A | 5/2000 | Oshida |
| 6,069,295 | A | 5/2000 | Leitao |
| 6,077,076 | A | 6/2000 | Comfort |
| 6,093,205 | A | 7/2000 | McLeod et al. |
| 6,113,640 | A | 9/2000 | Törmälä et al. |
| 6,121,172 | A | 9/2000 | Marcolongo et al. |
| 6,136,369 | A | 10/2000 | Leitao et al. |
| 6,143,948 | A | 11/2000 | Leitao et al. |
| 6,146,686 | A | 11/2000 | Leitao |
| 6,162,537 | A | 12/2000 | Martin et al. |
| 6,179,872 | B1 | 1/2001 | Bell et al. |
| 6,187,461 | B1 | 2/2001 | Lin et al. |
| 6,344,061 | B1 | 2/2002 | Leitao et al. |
| 6,384,195 | B1 | 5/2002 | Delgado et al. |
| 6,569,489 | B1 | 5/2003 | Li |
| 6,827,743 | B2 | 12/2004 | Eisermann et al. |
| 7,144,428 | B2 | 12/2006 | Anitua |
| 7,229,545 | B2 | 6/2007 | Sewing et al. |
| 7,368,065 | B2 | 5/2008 | Yang et al. |
| 2003/0125808 | A1 | 7/2003 | Hunter et al. |
| 2003/0176927 | A1 | 9/2003 | Steinemann et al. |
| 2004/0167633 | A1* | 8/2004 | Wen et al. .................. 623/23.57 |
| 2005/0043733 | A1 | 2/2005 | Eisermann et al. |
| 2005/0171604 | A1 | 8/2005 | Michalow |
| 2005/0251260 | A1 | 11/2005 | Gerber et al. |
| 2006/0018859 | A1 | 1/2006 | Carter |
| 2006/0105015 | A1 | 5/2006 | Perla et al. |
| 2006/0154206 | A1 | 7/2006 | Petersson |
| 2006/0289388 | A1 | 12/2006 | Yang et al. |
| 2006/0293758 | A1 | 12/2006 | Yang et al. |
| 2007/0260324 | A1 | 11/2007 | Joshi et al. |
| 2008/0044449 | A1 | 2/2008 | McKay |
| 2008/0081539 | A1* | 4/2008 | Ernsberger ...................... 451/28 |
| 2008/0241214 | A1* | 10/2008 | Myung et al. .................. 424/423 |
| 2009/0005868 | A1 | 1/2009 | Gundlapalli et al. |
| 2009/0008365 | A1 | 1/2009 | Tong et al. |
| 2009/0175918 | A1 | 7/2009 | Salvati et al. |
| 2009/0204213 | A1 | 8/2009 | Liao et al. |
| 2009/0266791 | A1 | 10/2009 | Yang et al. |
| 2010/0243429 | A1 | 9/2010 | Aoki et al. |
| 2010/0268227 | A1 | 10/2010 | Tong et al. |
| 2010/0268330 | A1 | 10/2010 | Tong et al. |
| 2010/0268346 | A1 | 10/2010 | Tong et al. |
| 2010/0268347 | A1 | 10/2010 | Tong et al. |
| 2011/0190902 | A1 | 8/2011 | Tong et al. |

FOREIGN PATENT DOCUMENTS

| | | |
|---|---|---|
| DE | 3414924 A1 | 10/1985 |
| DE | 19504386 A1 | 8/1996 |
| DE | 19811900 A1 | 9/1999 |
| DE | 19812713 A1 | 9/1999 |
| DE | 19812714 A1 | 9/1999 |
| EP | 0389713 A1 | 10/1990 |
| EP | 0838286 A1 | 4/1998 |
| EP | 1674051 | 6/2006 |
| EP | 1962894 A2 | 9/2008 |
| EP | 2072629 | 6/2009 |
| EP | 2093311 | 8/2009 |
| GB | 2045083 A | 10/1980 |
| WO | 9116012 A1 | 10/1991 |
| WO | WO-9203177 A1 | 3/1992 |
| WO | 92/05745 A1 | 4/1992 |
| WO | WO-9213984 A1 | 8/1992 |
| WO | WO-9218166 A1 | 10/1992 |
| WO | WO-9513101 A1 | 5/1995 |
| WO | WO-9817844 A1 | 4/1998 |
| WO | WO-9855053 A1 | 12/1998 |
| WO | WO-9930672 A2 | 6/1999 |
| WO | WO-9947082 A1 | 9/1999 |
| WO | WO-9962439 A1 | 12/1999 |
| WO | WO-02067824 A2 | 9/2002 |
| WO | 2005004941 A1 | 1/2005 |
| WO | WO-2007067744 A2 | 6/2007 |
| WO | WO-2007116690 | 10/2007 |
| WO | 2009075095 A1 | 6/2009 |

OTHER PUBLICATIONS

ASTM Designation: F 1537-00, "Standard Specification for Wrought Cobalt—28Chromium—6Molybdenum Alloys for Surgical Implants (UNS R31537, UNS R31538, and UNS R31539)," ASTM International (2003).

ASTM Designation: F 75-01, "Standard Specification for Cobalt—28 Chromium—6 Molybdenum Alloy Castings and Casting Alloy for Surgical Implants (UNS R30075)," ASTM International (2003).

Biomimetic Mineralization of Collagen by Combined Fibril Assembly and Calcium Phosphate Formulation, Jens-Hilmar Brat, et al. Chem. Mater. 1999, 11, 2694-2701.

Callaghan, "Ceramic-on-Polyethylene: Analysis of Results to Date", Seminars in Arthroplasty 14(2):86-88 (2003).

Collagen-Hydroxyapitate Composties for Hard Tissue Repair, DA Wahl and Czernuszka, European Cells and Materials vol. 11 2006, 43-56.

European Search Report, from corresponding EP Appl. No. 09158913.5, dated Oct. 7, 2009.

Euroean Search Report from corresponding EP Appl. No. 10159874.6, dated Jul. 26, 2010.

Goldsmith, A. at al., "A Comparative Joint Simulator Study of the Wera of Metal-on-Metal and Alternative Material Combinations in Hip Replacements," Institution of Mech. eng., J. of Eng. in Med. 214:39-47 (2000).

Liao, Y-S et al., Effects of Clearance, Head Size and Start-Stop Protocol on Wear of Metal-on-Metal Hip Joint Simulator, Ortho. Res. Soc., S.F., CA (2004).

U.S. Appl. No. 60/956,778, filed Aug. 20, 2007 to Salvati et al.

U.S. Appl. No. 12/696,880, filed Jan. 29, 2010 to Tong, et al.

Becker et al., "Proliferation and Differentiation of Rat Calvarial Osteoblasts on Type I Collagen-Coated Titanium Alloy," J. Biomed. Mater. Res. 59(3):516-27 (2002).

Beksac, B et al., "Surface finish mechanics explain different clinical survivorship of cemented femoral stems for total hip arthoplasty," J. Long-Term Effects Med. Implants 16(6):407-22 (2006).

Cheng, K. et al., "Osteolysis caused by tibial component debonding in total knee arthroplasty," Clin. Ortho.& Related Res. 443:333-36 (2006).

Conceicao, E. et al., "Chemical etching solutions for creating micromechanical retention in resin-bonded retainers," J. Prostetic Dentistry 71(3):303-09 (1994).

Coyle, T.W. et al., "Plasma Spray Deposition of Hydroxyapatite Coatings From Sol Precursors," Mat. Sci. Forum vols. 539-543 (2007) online at http://www.scientific.net.

Crowninshield, R. et al., "Cemented femoral component surface finish mechanics," Clin. Ortho.& Related Res. 355:90-102 (1998).

de Groot, K. et al., "New Biomimetic HA Coatings," Phosphorous Res. Bull. 6:71-74 (1996).

DePuy Spine, Inc., Helos Bone Graft Replacement, http://www.depuyspine.com/products/biologicssolutions/helos.asp.

Dowd, JE et al., "Failure of total hip arthroplasty with a precoated prosthesis," Clin. Ortho. & Related res. 355:123-36 (1998).

Extracellular Matrix (ECM), http://web.indstate.edu/theme/mwking/extracellularmatrix.html (Jan. 24, 2008).

Han, HS et al., "High incidence of loosening of the femoral component in legacy posterior stabilized-flex total knee replacement," J. Bone Joint Surg. 89B:1457-61 (2007).

Hydroxylapatite, http://en.wikipedia.org/wiki/Hydroxylapatite.

Kim, et al., "Preparation of Bioactive Ti and its Alloys Via Simple Chemical Surface Treatment," J. Biomed. Mat. Res. 32:409-17 (1996).

Kokubo, T. et al., "Spontaneous Formation of Bonelike Apatite Layer on Chemically Treated Titanium Metals," J. Am. Ceram. Soc. 79(4):1127-29 (1996).

Leitao, E. et al., "In Vitro Calcification of Orthopedic Implant Materials," J. Mat. Sci. 6(12):849-52 (Dec. 1995).

Leitao, E. et al., "Influence of Substrate Material and Surface Finishing on the Morphology of the Calcium-Phosphate Coating," J. Biomed. Mat. Res. 36:85-90 (1997).

Leitao, E., "Surface Modifications of Biomaterials vs. Biological Behavior," Univ. of Oporto (1996).

LifeNet Health, Safe and Effective Osteobiologic Options, www.accesslifenet.org/allograft_bioimplants/?family=1.

Mann et l., "Early cementing does not increase debond energy of grit blasted interfaces," J. Ortho. Res. 27:822-27 (2004).

Neto, HG et al., "Analysis of depth of the microporosity in a nickel-chromium system alloy—effects of electrolytic, chemical and sand-blasting etching," J. Oral Rehab. 30:556-58 (2003).

Pasteris, J. et al., "Apatite in Bone is Not Hydroxylapatite: There Must be a Reason," GSA Annual Meeting, Nov. 5-8, 2001, Paper 158-0, http://gsa.confex.com/gsa/2001AM/finalprogram/abstract_23719.htm.

Porocoat Porous Coating: For Use in Cementless Joint Replacement Surgery, Joint Replacement.com Restoring the Joy of Motion, http://www.jointreplacement.com/xq/ASP.default/pg.content/content_id.294/qx/default.htm.

Svehla et al., "No Effect of a Type I Collagen Gel Coating in Uncemented Implant Fixation," J. Biomed. Mater. Res. B Appl. Biomater. 74(1):423-28 (Jul. 2005).

Tanahashi, M. et al., Apatite Coating on Organic Polymers by a Biomimetic Process, J. Am. Ceram. Soc. &&(11):2805-08 (1994).

European Office Action and Search Report from corresponding EP Appl. No. 11151450.1, dated Sep. 20, 2011.

Research Discloser 293054, Process to enhance the adhesion of a polymer film to a steel alloy surface, Sep. 1988, p. 1. (Examiner Citation in pending related U.S. Appl. No. 12/754,340.

* cited by examiner

METHODS AND DEVICES FOR IMPLANTS WITH IMPROVED CEMENT ADHESION

CROSS REFERENCE TO RELATED APPLICATIONS

The present application is related to the following applications all filed on Apr. 15, 2009: (i) a U.S. Provisional Patent Application entitled "Micro and Nano Scale Surface Textured Titanium-Containing Articles and Methods of Producing Same," bearing Ser. No. 61/169,443; (ii) a U.S. Provisional Patent Application entitled "Nanotextured Cobalt-Chromium Alloy Articles having High Wettability and Method of Producing Same," bearing Ser. No. 61/169,365; (iii) a U.S. patent application entitled "Methods and Devices for Bone Attachment," bearing Ser. No. 12/424,000; and (iv) a U.S. patent application entitled "Methods and Devices for Implants with Calcium Phosphate," bearing Ser. No. 12/424,049. All four of these applications are hereby incorporated herein by reference in their entirety.

FIELD OF THE APPLICATION

The technical field of the present application is directed generally to manufactured substrates, and particularly to modifying such substrates to improve their characteristics for use as portions of a medical implant.

BACKGROUND

Medical implants for use as replacement structures in patients have become widespread in their application. In particular, orthopedic implants for replacing joints or other structures have received a great deal of attention commercially and scientifically. Oftentimes, orthopedic implants utilize a cement composition (e.g., a polymethyl methacrylate cement) to adhere the implant to bone. The bone/cement interface and cement/implant interface form two mechanical interlocking interfaces which are accountable for implant fixation.

The art generally recognizes that increasing the roughness of an implant surface, i.e., the arithmetic mean deviation of the surface profile, $R_a$, can result in a higher strength bond when cement is used to adhere the roughened surface to bone. Accordingly, enhanced cement/implant tensile strength bonding is often achieved by applying processes, such as grit blasting and/or glass bead shot blasting, to make progressively rougher implant surfaces In general, the relationship between increasing $R_a$ and increasing bond strength is linear. Roughened implant surfaces, however, can be detrimental with regard to abrasion processes. If an implant's mechanical interlocking to the bone cement (e.g., a hardened polymethyl methacrylate ("PMMA") composition) is not perfect, or degrades with time, relative movement (e.g., micromotion) between the bone cement and the implant can result in PMMA debris generation. While some believe a degree of micromotion is tolerable, PMMA debris has been found to be transported to the neighboring bone tissue, causing abnormal tissue response. Clinically, PMMA particles have been found to be directly associated with osteolysis around cemented hip stem implant. This threatens mid/long-term implant fixation. In general, rougher implant surfaces tend to result in higher debris generation (e.g., cement residues) and more trapped spaces in between PMMA cement and implant, which can decrease the ultimate fracture toughness of the bond. Thus, practitioners are faced with a tradeoff when deciding whether or not to increase the $R_a$ of an implant surface to improve implant fixation.

Accordingly, a need persists for implants and methods of treating such implants such that cement bond strength can be maintained at a high level, preferably without resulting in enhanced degradation due to abrasion-related processes.

SUMMARY

Some embodiments of the present invention are directed to methods for preparing a biomedical implant. A first roughened surface of the implant can be prepared, where the surface exhibits a first $R_a$ value that can be in the range from about 0.1 micron to about 100 microns. The first roughened surface can be exposed to a treatment formulation (e.g., an acid formulation that can optionally include a hydrohalic acid), which can form a second roughened surface that exhibits enhanced cement/implant mechanical interlocking upon contact with cement. For example, improved tensile fracture strength, improved shear fracture strength, or both with respect to a cement bond can be exhibited when the cement bond is formed between bone cement and the second roughened surface. The improvement can be relative to a cement bond formed between cement and the first roughened surface of the implant. In another example, improved tensile fatigue in tensile loading, improved fatigue in shear loading, or both can be exhibited when a cement bond is formed between bone and the second roughened surface of the implant, for example, relative to a cement bond formed between cement and the first roughened surface of the implant. In a third example, reduced abrasion of a cement bond formed between bone and the second roughened surface of the implant can be exhibited relative to a cement bond formed between bone and the first roughened surface of the implant.

Preparation of the first roughened surface can be performed by roughening a substrate surface using at least one of blasting, grinding, spraying, cast molding, and mechanical deformation. For example, particle blasting can be utilized, where the particles can optionally comprise at least one of an inorganic material and glass. In some instances, one or more particles from the blasting process can be embedded in the first roughened surface. In such instances, exposing the first roughened surface to the treatment formulation can result in removal of one or more particles from the first roughened surface.

The second roughened surface can exhibit one or more features as disclosed herein. For instance, the respective $R_a$ values of the first and second roughened surfaces can be substantially similar (e.g., the $R_a$ values can differ by less than about 20%). In another instance, the second roughened surface can be substantially free of particles from particle blasting. In yet another instance, the second roughened surface exhibits a surface coverage of non-native material from particle blasting of less than about 30% as measured by energy dispersive x-ray spectroscopy. In some instances, the second roughened surface can exhibit a lower $R_{sk}$ value relative to a $R_{sk}$ value exhibited by the first roughened surface.

In some instances, as part of a manufacturing method, an instruction can be provided regarding use of the implant such as an instruction to apply or contact a cement formulation to an implant surface (e.g., second roughened surface) to affix the implant in a subject.

Other embodiments of the present invention are directed to orthopedic implants, which can optionally be manufactured using one or more of the processes disclosed herein. The implant can include a surface modified to enhance fixation with cement. The implant surface, which can be a metallic surface such as a surface comprising a cobalt-chromium alloy, can be substantially free of a non-native material. The surface can also contact a cement formulation (e.g., a polymethyl methacrylate based cement). The implant surface can exhibit any number of features. For instance, the $R_a$ value of the implant surface can be between about 0.1 micron and about 100 microns. In another instance, the implant surface can exhibit a negative $R_{sk}$ value. In yet another instance, the implant surface can exhibit a surface coverage of less than about 30% by a material differing from the substrate material as measured by energy dispersive x-ray spectroscopy. In other instances, the implant surface can exhibit an average indentation diameter from about 0.1 microns and 20 microns; in some embodiments the indentation diameters can be interconnected or overlap to a degree.

Further embodiments of the present invention can be directed to methods of using an orthopedic implant. Such implants can include any of the implants disclosed herein, which can be produced using any of the manufacturing methods discussed. In some instances, an implant is provided having a surface modified to enhance fixation with cement that can be inserted into a subject. For instance, the implant can be attached to the bone of a subject using cement (e.g., a polymethyl methacrylate based cement). In another instance, the implant can be inserted into a sheath, where the combination of the sheath and the implant can act as a removable prosthetic in the subject. The implant surface can be substantially free of non-native material (e.g., particulates), can exhibit a $R_a$ value between about 0.1 micron and about 100 microns, and/or a negative $R_{sk}$ value, and/or exhibit an average indentation diameter from about 0.1 microns and 20 microns in which the indentations can optionally overlap to a degree.

BRIEF DESCRIPTION OF THE DRAWINGS

Aspects of the present invention will be more fully understood from the following detailed description taken in conjunction with the accompanying drawings (not necessarily drawn to scale), in which.

DETAILED DESCRIPTION OF EMBODIMENTS

Figure 1A:
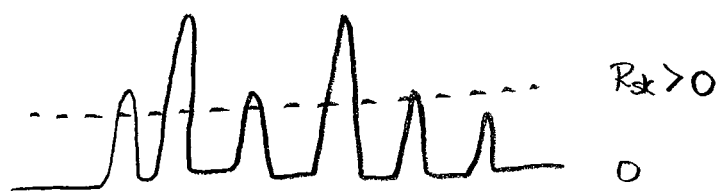
FIG. 1A is schematic side view diagram of a roughened surface exhibiting a positive $R_{sk}$ value.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Embodiments of the present invention can be directed to implants, kits including implants, and methods of forming implants, which can be inserted into a subject to act as a structural replacement (e.g., a joint replacement). Such implants can have a surface that enhances the strength of a cement bond (e.g., a cement that includes polymethyl methacrylate ("PMMA")), which can act to fix an implant to a portion of the subject (e.g., the bone of a subject). The strength of the cement bond between the implant and subject can be characterized by any one, or more, of a tensile strength, a shear strength, a torsional strength, a tensile fatigue characteristic (e.g., failure strength and/or number of cycles to failure), a shear fatigue characteristic, and a torsional fatigue characteristic. The enhancement of the cement bond strength of the implant can be relative to the cement bond strength associated with an implant surface prepared by a prior art process (e.g., a surface grit blasted with alumina, silica, zirconia, and/or other particles). The surface of such implants can be characterized by any number of physical, chemical, or process-derived properties such as having a roughness characterized by a particular range of values of $R_a$ (e.g., from about 0.1 micron to about 100 microns) and/or exhibiting a plurality of indentations (e.g., overlapping) having an average diameter of about 0.1 micron to about 20 microns, and/or a $R_{sk}$ (e.g., have a negative value).

Some particular embodiments are drawn to preparing such implants using a process in which a first roughened surface is provided exhibiting an initial $R_a$ value (e.g., from about 0.1 micron to about 100 microns). This first surface can be provided using a conventional surface roughening method such as grit-blasting or other type of mechanical roughening mechanism. The first roughened surface can be exposed to a treatment formulation (e.g., an acid formulation) to provide a second roughened surface that exhibits enhanced cement fixation properties relative to the first roughened surface. The second roughened surface can exhibit any number of chemical and/or physical characteristics. For example, the second roughened surface can have a $R_a$ value that is substantially similar to the first roughened surface, the $R_{sk}$ value of the second roughened surface can be less than the $R_{sk}$ value of the first roughened surface, and/or the $R_{sk}$ value of the second roughened surface can be negative.

Implants consistent with some of the embodiments discussed herein can exhibit advantageous properties relative to previously manufactured implants. For instance, when a conventional grit blasting or other roughening technique is used to provide an initial roughened surface for an implant, the treated roughened surface can provide a stronger cement bond while not changing the $R_a$ value of the surface substantially. This can help reduce the effect of enhanced abrasion and/or loss of fatigue that is typically associated with increasing roughness of a surface to provide better cement bonding. As well, the enhancement in bond strength can be significant; the enhancement in any of tensile strength, shear strength, torsional strength, or some characteristic of fatigue between the first and second roughened surfaces can be greater than about 10%, 20%, 30%, 40%, 50%, 60%, 80%, 100%, 120%, 140%, 160%, 180%, 200%, 220%, 240%, 260%, 280%, or 300%, or greater, lesser, or intermediate percentages. Thus, these embodiments can exhibit unexpected changes in cement bond strength that are highly non-linear relative to a surface implant's $R_a$, in contradiction with the conventionally understood effect.

Implant Properties and Surface Characterization

Implants consistent with embodiments of the present application can be formed from a substrate having a surface that is modified in some manner to exhibit enhanced cement bonding strength. The composition of the substrate and/or the surfaces of the substrate can be anything suitably consistent with the embodiments described herein. Materials such as metals, ceramics, polymers, and other materials, including composites of materials, can be utilized. In some embodiments, the surfaces of the substrate can be metallic. In general, the term "metallic" is used to describe an object having at least some qualities of bulk metals. Accordingly, metallic surfaces and substrates exhibit at least one property similar to that of bulk metals. For example, non-metallic materials that have trace contaminants of metal impurities can be excluded from a description of metallic surfaces and substrates. Examples of metallic materials used for implants can include those suitable for medical implantation within a subject, such as stainless steel (e.g., 316L), titanium-based materials, titanium-based alloys (e.g., Ti6Al4V), and chromium-based alloys (e.g., a cobalt-chromium alloy or a cobalt-chromium-molybdenum alloy). Examples of cobalt-chromium alloys include alloys consistent with ASTM standard F 1537-00 and F 75-01, and cobalt chromium molybdenum alloys having substantially higher than about 25% chromium (e.g., chromium in a range from about 26% to about 30%) and higher than about 3% molybdenum (e.g., molybdenum in a range from about 5% to about 7%).

Fixation of the implants disclosed herein can utilize a cement formulation which contacts a surface of the implant and a portion of a subject (e.g., a bone of the subject). Accordingly, many embodiments of the present invention are directed to the use of a cement that forms a bond between an implant and a subject's bone. While any suitable cement can be used to fix the implant, some embodiments of the invention utilize an acrylic-based cement such as a cement formulation comprising a polymethyl methacrylate based resin ("PMMA"). The cement can be formed by mixing a liquid monomer component with a solid polymer component (e.g., a PMMA cement is typically formed from PMMA particles mixed with liquid monomer). Other components such as polymerization initiators, radio-opacifier (e.g., zirconia and/or barium sulfate), and/or bioactive components such as antibiotics can optionally be included.

As discussed herein, implants and processes for preparing such implants can involve an implant surface which can exhibit enhanced cement bonding strength. Accordingly, the implant surface can have one or more chemical, physical, and/or process-derived characteristics which can contribute to the enhancement of cement bonding strength. While some embodiments discussed herein refer to particular surface characteristics that can be linked with enhanced cement bonding strength, it is understood that not all embodiments are limited to implants bearing such characteristics. For instance, in some embodiments, the manufactured implant's characteristics can be attributed to the manufacturing process, and is not necessarily linked with one or more of the implant characteristics explicitly discussed herein.

In some embodiments, the enhanced cement bonding strength associated with an implant's surface can attributed, at least in part, to the roughness of the implant's surface. In some embodiments, an implant surface's roughness can be characterized by one or more roughness values as defined herein. As utilized herein, roughness values (e.g., $R_a$) and other roughness measures having a length scale are characterized in units of microns, unless otherwise explicitly stated.

In one instance, the roughness of a surface can be characterized by a $R_a$ value, where $R_a$ is mathematically defined as:

$$R_a = \frac{1}{L}\int_0^L \|y - Y\| dx$$

where, L is the length of the sample being characterized by the value, y is the height at a given position, and Y is the mean height along the length L of the sample. In a discrete mathematical calculation, $R_a$ is given by $$R_a = \frac{1}{N}\sum_{i=1}^{N} \|y_i - Y\|$$

where N is the total number of discrete measurements in the calculation and $y_i$ is the value of the height of the ith measurement. Accordingly, $R_a$ provides a measure of the arithmetic average deviation from a centerline roughness profile over a given sample length.

The roughness of a surface can also be characterized by a $R_q$ value, where $R_q$ is mathematically defined as:

$$R_q = \frac{1}{L}\int_0^L \sqrt{(y - Y)^2}\, dx$$

or in terms of performing a discrete calculation $$R_q = \frac{1}{N}\sum_{i=1}^{N} \sqrt{(y_i - Y)^2}$$

Accordingly, $R_q$ provides a measure of the root mean square deviations from a centerline roughness profile over a given sample length.

Another characterization of roughness can be provided by a $R_z$ value, where $R_z$ is mathematically defined as:

$$R_z = \frac{1}{5}\left(\sum_{i=1}^{5} yp_i + \sum_{j=1}^{5} yv_j\right)$$

where over a sampled length L having a mean height Y, $yp_i$ is ith highest peak above Y recorded over the length L, and $yv_j$ is the jth lowest valley below Y recorded over the length L Accordingly, $R_z$ provides a measure of the arithmetic average deviations from a centerline roughness profile using the five highest measured peaks and the five lowest measured valleys over a selected length L.

Surface roughness can also be characterized by a $R_{sk}$ value, where $R_{sk}$ is mathematically defined as:

$$R_{sk} = \frac{1}{R_q^3}\int_0^L Z^3 P(z) dz$$

which is the third degree moment of the amplitude density function of a length L divided by the cube of $R_q$, or in terms of a discrete calculation:

$$R_{sk} = \frac{1}{NR_q^3}\sum_{i=1}^{N}(y_i - Y)^3$$

Figure 1B:
FIG. 1B is schematic side view diagram of a roughened surface exhibiting a negative $R_{sk}$ value.

Accordingly, $R_{sk}$ characterizes the asymmetry of a surface. For instance, for a roughened surface where the features are characterized as protrusions from a planar surface, as depicted in FIG. 1A, the $R_{sk}$ value is greater than zero. A negative $R_{sk}$ value, i.e., less than zero, indicates that the valleys of the surface are more prominent than the peaks. An example of such a surface is depicted in FIG. 1B, where the features of the surface are generally valleys into a planar surface. In general, a surface having a negative $R_{sk}$ value can be said to exhibit negative draft, and can typically act as a better lubrication surface.

It should be noted that $R_a$ values, as well as other roughness values, can display a substantial dispersion of values even for similarly prepared samples as recognized by those skilled in the art. In accord, and as utilized throughout the present application, two roughness values (e.g., $R_a$ values) are considered "substantially similar" when their values are within about 30% of each other, i.e., the absolute value of the difference of the roughness values divided by the smaller roughness value is a value no larger than about 0.3. In other embodiments, two roughness values can be within about 25%, 20%, 15%, 14%, 13%, 12%, 11%, 10%, 9%, 8%, 7%, 6%, 5%, 4%, 3%, 2%, 1%, or more or less or intermediate percentages of each other.

An actual experimental determination of the roughness value of a surface can be performed in a variety of different manners including utilizing techniques known to one of ordinary skill in art. As used throughout the present application, $R_a$ values can be determined with a typical measurement device such as a contact profilometer using a standard diamond stylus having a tip size no smaller than 1.5 microns in radius. In some embodiments, the $R_a$ values can be determined using a standard diamond stylus having a tip size no smaller than about 2 microns in radius. For example, the $R_a$ values in the Examples section herein were measured using a Zeiss Surfcom 5000 contact profilometer using TiMS software and a diamond tip of 1.5 to 2 micron radius tip. The sample length was typically 0.8 mm and the evaluation length is 0.8 mm×5 (i.e., five sample lengths of 0.8 mm were used to evaluate a given $R_a$ value).

Likewise, values of $R_q$, $R_z$, and $R_{sk}$ can be evaluated in a variety of manners. In many of the embodiments disclosed herein, actual measurements of $R_q$, $R_z$, and $R_{sk}$ are evaluated in a similar manner as $R_a$ (e.g., using a contact profilometer having a diamond stylus with a tip radius no smaller than about 1.5 microns, or no smaller than about 2 microns, or some intermediate value). In general, roughness values associated with embodiments herein are evaluated in accord with the ASME95 standard.

Figure 2:
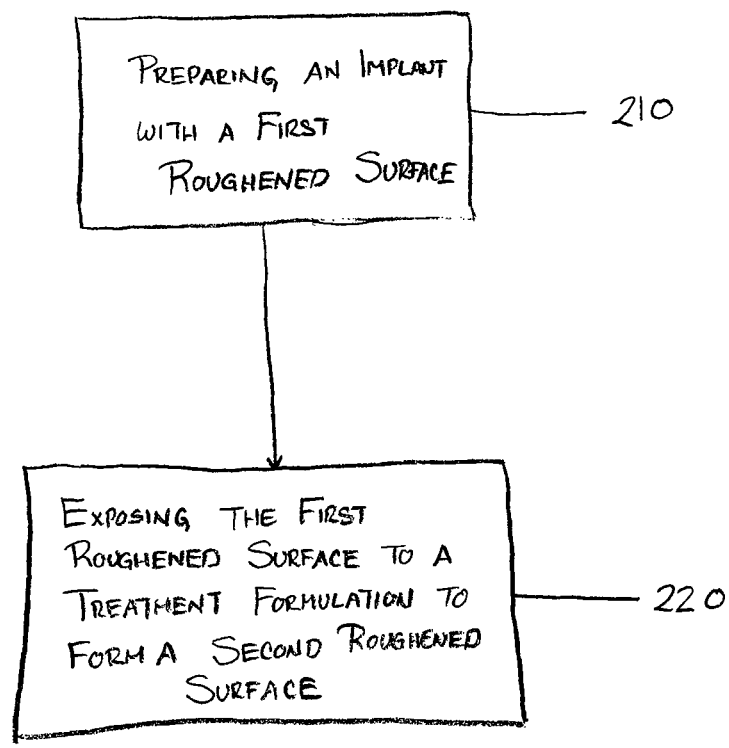
FIG. 2 presents a flow diagram of a method for producing an implant consistent with some embodiments of the present invention.

Accordingly, in some embodiments, an implant surface that exhibits enhanced cement bonding characteristics can be characterized by at least one of a $R_a$, $R_q$, and $R_z$ value in a range from about 0.1 micron to about 100 microns. In other embodiments, the lower value of the range can be about 0.5 micron or about 1 micron; the higher value of the range can be about 50 microns or about 10 microns. As well, or in addition, the implant surface can be characterized by a negative $R_{sk}$ value. While not being bound by any particular theory, it is conjectured that for some embodiments an implant surface having a $R_a$, $R_q$, or $R_z$ value as disclosed herein with a negative $R_{sk}$ value and/or overlapping indentation diameters in a range from about 100 nm to about 20 microns can aid in cement adhesion. For instance, a $R_a$ value can characterize the average surface profile height over length. The more negative $R_{sk}$ intuitively allows closer contact of PMMA cement to the surface, leaving a smaller gap between cement and substrate surface, see e.g., the more negative $R_{sk}$ value surface depicted in FIG. 2 vis-à-vis the surface depicted in FIG. 1. Other potential advantages can be that $R_a$ value can be sufficient to allow for adequate cement bond tensile strength, while the negative $R_{sk}$ value can contribute to inhibiting the creation of cement residues when relative movement exists between an inserted implant and the cement, which can generate wear PMMA particles and cause unfavorable osteolysis.

Roughness of a surface can also be characterized by other geometrical considerations such as an average indentation diameter. Accordingly, in some embodiments, an implant surface can be characterized by an average indentation diameter in a range from about 0.1 micron to about 500 microns. The lower bound can also be about 0.2 micron, 0.5 micron, 1 micron, or larger, smaller, or intermediate values. The higher bound can also be about 200 microns, about 100 microns, about 50 microns, about 40 microns, about 30 microns, about 20 microns, about 15 microns, about 10 microns, about 5 microns, about 4 microns, about 3 microns, about 2 microns, about a micron, or larger, smaller, or intermediate values. Accordingly the average indentation diameter can be in a range using any suitable combination of the lower bound and upper bound disclosed herein. The average size opening refers to the average characteristic length scale of a selected set of surface pit openings. If all the surface openings are perfectly circular, the average size opening is the average diameter of the openings. When the surface openings are not uniform in geometry, the average size opening can have a value as understood by those skilled in the art. For instance, the average size opening can be the average effective diameter, $\epsilon$, of the size openings (e.g., $\epsilon$ can be defined by the relationship $\epsilon=2(\Delta/\pi)^{1/2}$, where $\Delta$ is the area of an opening).

Measurement of one or more surface characteristics to derive the size of a pit opening or other physical surface aspect (e.g., roughness, pit size, surface area, etc.) can be achieved using any of the techniques known to one skilled in the art. In some instances, the surface pit can be characterized by using images obtained from techniques such as transmission electron microscopy or scanning electron microscopy. The images can be analyzed using conventional image analysis to obtain sizes such as pit opening dimensions. Other techniques can also be used such as atomic force microscopy, also known as scanning force microscopy.

In some embodiments, the properties of indentations (e.g., opening size) of an implant surface can be limited to indentations exhibiting a particular aspect ratio or a grouping of indentations exhibiting a particular average aspect ratio The aspect ratio of an indentation is defined as the ratio of the major axis dimension (i.e., the largest spatial dimension) of an indentation divided by the minor axis dimension of an indentation (i.e., the spatial dimension of perpendicular line drawn at a point along the major axis line corresponding with the largest special extent of the indentation along that minor axis). Accordingly, the average aspect ratio is the numerical average of all the individual aspect ratios in a selected set. In some embodiments, the aspect ratio, or the average aspect ratio, can be less than about 200, 100, 50, 40, 30, 20, 10, 5, 4, 3, 2, or 1.5. Thus, in some embodiments, the indentations can be limited to features that do not appear as long or especially elongated cracks or crevices.

In some embodiments, the indentations of an implant surface can exhibit an overlapping nature, i.e., a plurality of the indentations are interconnected with one another. In such embodiments, the opening size of an indentation can be determined by interpolating the area that an individual opening would have if the overlapping indentation(s) were not present. While not being limited by any particular theory, it is believed that interconnected indentations can be formed as a result of an etching process initiated by the implant surface being exposed to a treatment formulation as disclosed herein. The number of overlapping indentations may be more numerous than exhibited by indentations formed by a grit-blasting process alone. In some embodiments, the percentage of the total number of indentations in an area that are overlapping can be greater than about 50%, 60%, 70%, 75%, 80%, 85%, 90%, 95%, 96%, 97%, 98%, 99%, or more or less or intermediate values.

As discussed above, other physical, chemical, and/or process-derived characteristics can be attributed to an implant surface, besides roughness, which can at least in part contribute to enhanced cement bond strength. For instance, the surface of the implant can be substantially free of the presence of a non-native material. As utilized in the present application, the phase "non native material" in the context of an implant surface refers to a material that differs in nature from the substrate surface used to form the implant surface. For example, if a metallic substrate surface is impacted with ceramic particles to form a roughened surface, the roughened surface may have ceramic particles embedded therein, i.e., the metal of the metallic surface is the native material and the ceramic is the non-native material.

Furthermore, an implant surface that is "substantially free" of non-native material, as used in the present application, refers to an implant surface with areal coverage of less than 40% by the non-native material. In some embodiments, the coverage of an implant surface by a non-native material can be less than about 35%, 30%, 25%, 20%, 15%, 10%, 8%, 7%, 6%, 5%, 4%, 3%, 2%, 1%, 0.5%, or less, or more, or intermediate percentages. While the surface coverage of non native material can be determine using any number of methodologies, including those known to one skilled in the art, in some embodiments the surface coverage can be determined using energy dispersive x-ray spectroscopy. Another potential method is X-ray photoelectron spectroscopy.

While not being bound by any particular theory, it is believed that in some embodiments the presence of surface pits/indentations, either by removal of a non-native material on an implant surface and/or surface etching as can be effected by a treatment formulation, can promote cement bond strength. For instance, the presence of aluminum oxide particles on an implant surface (e.g., due to grit blasting to form a roughened surface) can inhibit direct cement/implant mechanical interlocking. Accordingly, the removal of such particles is believed to substantially enhance cement bond strength.

Use of implants consistent with embodiments disclosed in the present application can include providing an implant having a surface with any number of the features and characteristics described in the present application (e.g., an implant surface exhibiting a $R_a$ value in a range from about 0.1 micron to about 100 microns and a negative $R_{sk}$ value). The implant can then be inserted into a subject, where a cement formulation (e.g., a PMMA reacting formulation) can be contacted to a surface of the implant and/or bone. Curing of the formulation, which can involve the application of radiation, can result in hardening of the cement, and thereby fixation of the implant to a subject's bone.

In some embodiments, implants consistent with those disclosed in the present application can be included as a portion of a kit, which can be provided to distributors and/or users. The kit can have one or more of such implants, and can include an instruction regarding the use of such an implant. For example, the instruction can direct a user to apply a cement formulation to a surface of the implant (e.g., the second roughened surface) for affixing the implant to a bone or other portion of a subject's body. The kit can optionally include other materials such as cement formulation components and/or other surface preparation materials for preparing the implant for insertion into a subject. All such possible combinations are within the scope of the present invention.

In some embodiments, implants described in the present application can be implanted in a subject either using cement or other technique(s). For instance, an implant consistent with some embodiments (e.g., an implant having a surface characterized by a $R_a$ value in a range from about 0.1 micron to about 100 microns and a negative $R_{sk}$ value) can be part of a kit including instructions which can indicate that the implant can be fixed in a body by using a cement, and/or by insertion in a covering (e.g., a sleeve) in which the ensemble is inserted into a subject. The latter option can allow for easier removal of the implant at a later time, and can exclude the use of cement in its implantation process.

Currently, two different implants are required for each of the aforementioned insertion techniques. An implant intended for cement fixation would typically use a surface having a different (e.g., higher) $R_a$ relative to the implant intended for use with a covering. The $R_a$ of the cement-intended implant is tailored for cement bond strength while the $R_a$ of the covering-intended implant is lower and tailored for a selected friction between the covering surface and the implant surface. An implant consistent with embodiments herein can have a surface with a lower $R_a$ for use with coverings, while maintaining the ability to form a cement bond with higher strength relative to conventional cemented implants exhibiting the same lower $R_a$. Accordingly, implants consistent with embodiments herein can be suited for both implantation usages, which can reduce the manufacturing and logistical burdens associated with inventorying two different types of implants.

It is understood that structures consistent with the embodiments disclosed herein only represent some embodiments of the present invention. Indeed, any permutation and combination of the features as disclosed in the description in the present application can be assembled to practice an embodiment consistent with some aspects of the present invention. Other embodiments can include other features, or present modification(s) and/or variation(s) to the features of the embodiments disclosed herein. Some of the aspects of the embodiments are elaborated in further detail herein with respect to the processes that can be employed to produced such implants. Any number of the aspects discussed with respect to an element can be assembled with other elements, or practiced individually, consistent with the scope of the present invention.

Methods for Producing Implant Surfaces Exhibiting Enhanced Cement Fixation

Some embodiments of the present invention are directed to methods of preparing an implant with a surface exhibiting enhanced cement bond strength. While such methods can be used in some instances to produce some of the implants disclosed herein, it is understood that the methods are not necessarily restricted to those implants. Some particular embodiments of such preparation methods can be described with reference to the flow chart depicted in FIG. 2. In general, a first roughened surface of an implant is prepared 210, where the surface can be characterized by a roughness value such as an initial $R_a$ value. The first roughened surface is exposed to a treatment formulation to form a second roughened surface 220. The second roughened surface can enhance the strength of a cement bond formed between the second roughened surface a portion of a subject (e.g., the subject's bone) relative to a cement bond formed between an implant having the first roughened surface and the subject. Optionally, the process can utilize post treatment steps such as water rinsing and/or ultrasonication to further remove residues.

Preparation of the first roughened surface 210 can be performed in any number of manners. In some embodiments, a substrate surface can be created with, or modified into, a first roughened surface using any number of mechanical transformative techniques. Non-limiting examples include particle blasting, surface grinding or abrasion with solids and/or liquid mixtures, spraying, cast molding, and other mechanical deformation techniques including those known to one skilled in the art. Appropriate chemical techniques, among others, can be used in addition, or alternatively, as understood by those skilled in the art.

In particular embodiments, particle blasting is utilized to form the first roughened surface. This process can be consistent with prior art processes for roughening metal implant surfaces. While any number of types of particulates/grit can be used to form the roughened surface, many embodiments utilize a non-native material (i.e., a material having a different chemical character than the material of the substrate surface being blasted). Blasting particles can be formed from a variety of materials such as inorganic materials such as zirconium dioxide and/or aluminum oxide, or glass (i.e., silica). Other types of particles include water soluble particles such as sodium chloride or sodium bicarbonate, calcium phosphate with any combination of calcium of phosphate ratio, or combinations of such materials. Particle sizes can range from about 10 micron to about 10 mm, and blasting can occur at a pressure of 1 PSI to 200 PSI. When such embodiments are utilized, the first roughened surface can often have residual blasting particles embedded or otherwise disposed on the surface. In some instances, the areal coverage of the particles can be at least about 30%, 40%, 50%, or more (e.g., as determined by energy dispersive x-ray spectroscopy).

The roughness of the first roughened surface can be characterized by one or more roughness values, including those described in the present application. For instance, in some embodiments, the first roughened surface can be characterized by at least one of a $R_a$, $R_q$, and $R_z$ value in a range from about 0.1 micron to about 100 microns. In other embodiments, the lower value of the range can be about 0.5 micron or about 1, or about 10 microns; the higher value of the range can be about 50 microns. The roughness of the surface can also be characterized by other features (e.g., an average indentation diameter), which can or cannot be consistent with features of a final implant surface as described herein.

In forming the second roughened surface by exposing the first roughened surface to a treatment formulation 220, a number of different types of formulations can be utilized to enhance the cement bonding properties of the second surface relative to the first. Exposure to the treatment formulations can modify a first roughened surface physically, chemically, or in both manners, which can result in the enhancement of cement bonding strength. In some embodiments, these formulations can be chosen to impart such characteristics based upon the nature of the substrate surface exposed. For example, the formulations can be specially tailored to impart chemical/mechanical characteristics to metallic substrates, which can be titanium alloys and/or chromium-based alloys.

In some embodiments, the treatment formulation comprises an etching formulation, which can modify the first roughened surface. For instance, the formulation can be an acid formulation. Acid formulations can include formulations that create a microetch-morphology on a metallic substrate surface, such as disclosed in U.S. Pat. No. 7,368,065, which is incorporated herein by reference it its entirety. Alternatively, a formulation can be used that would create a nanoetch morphology on some metallic substrates such as on a titanium alloy or cobalt-chromium alloy surface. A description of such formulations is provided in two U.S. patent applications that were concurrently filed on Apr. 15, 2009: (i) a U.S. Provisional Patent Application entitled "Micro and Nano Scale Surface Textured Titanium-Containing Articles and Methods of Producing Same," bearing Ser. No. 61/169,443; and (ii) a U.S. Provisional Patent Application entitled "Nanotextured Cobalt-Chromium Alloy Articles having High Wettability and Method of Producing Same," bearing Ser. No. 61/169,365. Both these application are hereby incorporated by reference in their entirety.

In particular embodiments, the acid formulation can include a hydrohalic acid, for instance a hydrohalic acid that substantially excludes hydrofluoric acid. As well, such formulations can also be substantially free of other potentially hazardous components such as aqua regia and/or methanol. The hydrohalic acid (e.g., HCl, HBr, HI, or some combination thereof), which can be at a concentration of 1M to 12M, can include other components such as halogen-containing salts having a different character than the hydrohalic acid (e.g., a chlorine containing salt), an oxyacid (e.g., a phosphoric oxyacid), and a phosphate containing salt. In some embodiments, the acid formulation can also include an oxidant such as hydrogen peroxide, ammonium persulfate, or other appropriate oxidizing agent.

In other embodiments, the acid formulation can be include a hydrohalic acid (e.g., any one or a combination of HCl, HBr, HI, and others) that is substantially free of an oxidant (e.g., the presence of any oxidant does not affect the performance of the formulation in modifying an exposed surface). The concentration of the acid can be in a range from about 1N to about 12N. Formulations can also include other components, such as halogen-containing salts or other agents which can be soluble in the acid formulation.

For instance, in some treatment formulations being applied to a cobalt chromium alloy substrate surface, the acid formulation has a concentration of $H^+$ of at least about 4 N and a concentration of halide (e.g., $Cl^-$) of at least about 4 N. The formulation can further comprise a chloride-containing compound, or other halide-containing compound, differing from the acid at a concentration in the range of about 0.01N to 8N. In some embodiments, the formulation has a concentration of $H^+$ of about 0.8 to about 12N and a concentration of $Cl^-$ that is greater than said concentration of H. Examples of chloride-containing compounds include sodium chloride (NaCl), potassium chloride (KCl), calcium chloride ($CaCl_2$), ammonium chloride ($NH_4Cl$), ferric chloride ($FeCl_3$), ferrous chloride ($FeCl_2$), cobalt chloride ($CoCl_2$), magnesium chloride ($MgCl_2$) and mixtures thereof.

In treatment formulations being applied to titanium containing substrate surfaces, the acid formulation can have a concentration of $H^+$ of at least about 0.07 N and a halide concentration (e.g., $Cl^-$) of at least 6N. In some processes, the solution has a concentration of $H^+$ of at least about 0.07 N and a halide concentration (e.g., $Cl^-$) greater than the concentration of $H^+$. The formulation can further comprise a chloride-containing salt or other halide-containing salt at a concentration in the range of about 0.01 N to 10 N. In some embodiments, the formulation has a concentration of $H^+$ of about 0.07 to about 12N and a concentration of $Cl^-$ that is greater than the concentration of $H^+$.

In some instances, the substrate surface can be exposed to a formulation for a period of time sufficient to create a desired modification (e.g., average opening size and/or average depth). In some embodiments, the exposure of any single formulation is less than about 24 hours, or less than about 12 hours, or less than about 6 hours, or less than about 2 hours, or less than about 1 hour. The exposure time can be greater than about 2 minutes, 5 minutes, 10 minutes, 15 minutes, 20 minutes, or 30 minutes. In some particular embodiments, the exposure period can be longer than about 30 minutes and shorter than about 24 hours.

In some embodiments, the formulation can be utilized under reasonable thermal conditions, in which the formulation can be stable (i.e., not susceptible to combustion). For instance, the formulation can be used at a temperature greater than about 10° C. but less than about 30° C., 40° C., 50° C., 60° C., 70° C., 80° C., 90° C., or 100° C. For example, the formulation is kept at a temperature between about 15° C. and about 30° C., or between about 20° C. and about 40° C., during exposure.

As previously stated, exposure of the first roughened surface to the treatment formulation can result in physical modification, chemical modification, or both, which can result in the enhancement of cement bonding strength of the modified surface. In some embodiments, the $R_a$ value of the first and second roughened surfaces are substantially similar, or within about 25%, 20%, 15%, 14%, 13%, 12%, 11%, 10%, 9%, 8%, 7%, 6%, 5%, 4%, 3%, 2%, 1%, or more or less or intermediate percentages of each other. Other physical changes can be possible, however. For instance, the treatment formulation can result in a $R_{sk}$ value of the second roughened surface being negative, and/or being lower than a $R_{sk}$ value of the first roughened surface. The degree of lowering of a $R_{sk}$ value between a first and second roughened surface by a treatment formulation can vary. In some embodiments, the drop can be more than about 25%, 50%, 75%, 100% or more relative to the absolute value of the $R_{sk}$ value of the first roughened surface.

Without being bound by any particular theory, in some instances it is believed that the lowering of a $R_{sk}$ value can be due to the removal of embedded particles in a first roughened surface, such as non-native particles from a particle blasting step, by the action of the treatment formulation. Accordingly, the removal of such particles can result in a $R_{sk}$ lowering without a substantial change in the $R_a$ value. Thus, it can be conjectured that more surface area for cement fixation can be created while not resulting in a substantially higher $R_a$ which can degrade abrasion resistance.

In related embodiments, a treatment formulation can result in the second roughened surface being substantially free of a non-native material, e.g., having an areal coverage of non-native material less than about 35%, 30%, 25%, 20%, 15%, 10%, 8%, 7%, 6%, 5%, 4%, 3%, 2%, 1%, 0.5%, or less, or more. As mentioned earlier, the removal of particles, such as aluminum oxide particles such that the surface is 90% or more clear of non native particles, can result in an enhancement of cement bond strength.

In some embodiments, exposing a first roughened surface to a treatment formulation can result in a second roughened surface with substantially better cement bonding strength without some of the physical changes described in other embodiments herein. For instance, a chromium-cobalt alloy substrate was prepared by roughening its surface by particle blasting with zirconia with a small amount of zirconia residue embedded in the blasted surface. Subsequent acid formulation exposure to the surface provided somewhat unclear evidence as to how much non native particle material was removed. $R_{sk}$ values associated with the first roughened surface and the second roughened surface were transformed into more negative values after second roughening treatment when the first roughened surface had a $R_{sk} > -0.5$. When the first roughened surface has $R_{sk} < -0.5$, the second roughened surface may have smaller or a non-statistically significant change of $R_{sk}$. Nonetheless, tensile strength of a cement bond increased by about 250% to about 300% in the second roughened surface.

Without being bound by any particular theory, a topographical change of peak distribution (i.e. $R_{sk}$) and/or removal of residues and/or addition of surface pits/indentations to the first roughened surface may be responsible for the augmentation of bond strength, e.g., resulting in a high attraction between a PMMA based cement and the chromium-cobalt metal surface. Such changes can be due to the exposure of a treatment formulation to the first roughened surface resulting in the creation of pits and indentations (e.g., overlapping indentations having an average diameter of about 100 nm to about 20 microns). The changes can occur with or without the removal of blasting particles or other non-native particles.

In some embodiments, exposing a first roughened surface to a treatment formulation can result in second roughened surface exhibiting etched features relative to the first roughened surface. For instance, a treatment formulation, such as an acid formulation, can act to etch the first roughened surface to provide morphological changes such as creating additional indentations and altering the shape of preexisting indentations. In some embodiments, the additional features created by an etching solution can result in a surface with substantially similar $R_a$ values, and the $R_{sk}$ value can optionally become more negative.

In preparing implants in accord with some embodiments herein, a producer can include an instruction regarding the use of such implants with a product. Accordingly, in some instances, a method of preparing an implant can include providing an instruction for use of the implant such as an instruction to contact cement with an implant surface (e.g., a second roughened surface of the implant) to affix the implant in a subject.

EXAMPLES

The following examples are provided to illustrate some embodiments of the invention. The examples are not intended to limit the scope of any particular embodiment(s) utilized.

Example 1

Zirconia Blasted Substrates—Control and Treated

Cast cobalt-chromium-molybdenum (ASTM F75) rod stock (0.75" diameter and several feet long) were machine cut to 0.75" (diameter)×1.5" (length) cylinders. The test surface was buffed ($R_a < 0.2$ micron) before zirconia blasting ("Zr blasted") to remove artifacts of machining. The test cylinders were particle blasted with zirconium dioxide beads of B60 grit at typical room conditions using a work distance of about 4 to 8 inches at 40 PSI for a blasting time of about 5 to about 30 seconds. The blasted surfaces were blown clean with compressed air followed by ultrasonic cleaning in detergent (1-2% Alconox) and reverse osmosis ("RO") water. The surfaces were then dried at 60° C.

A number of these samples were reserved for testing; these were designated as control samples. The remaining samples were further treated with a 8N hydrochloric acid solution at a room condition of 18-23° C. for a period of 24 hours. The test cylinders were subsequently rinsed in RO water, ultrasonically cleaned in RO water for 20 minutes, then ultrasonically cleaned in RO water for 10 minutes and 5 minutes with interstitial rinsings in RO water. The cylinders are then dried at 60° C. for at least 2 hours in an oven. The acid treated samples were designated as treated samples.

Figure 3A:
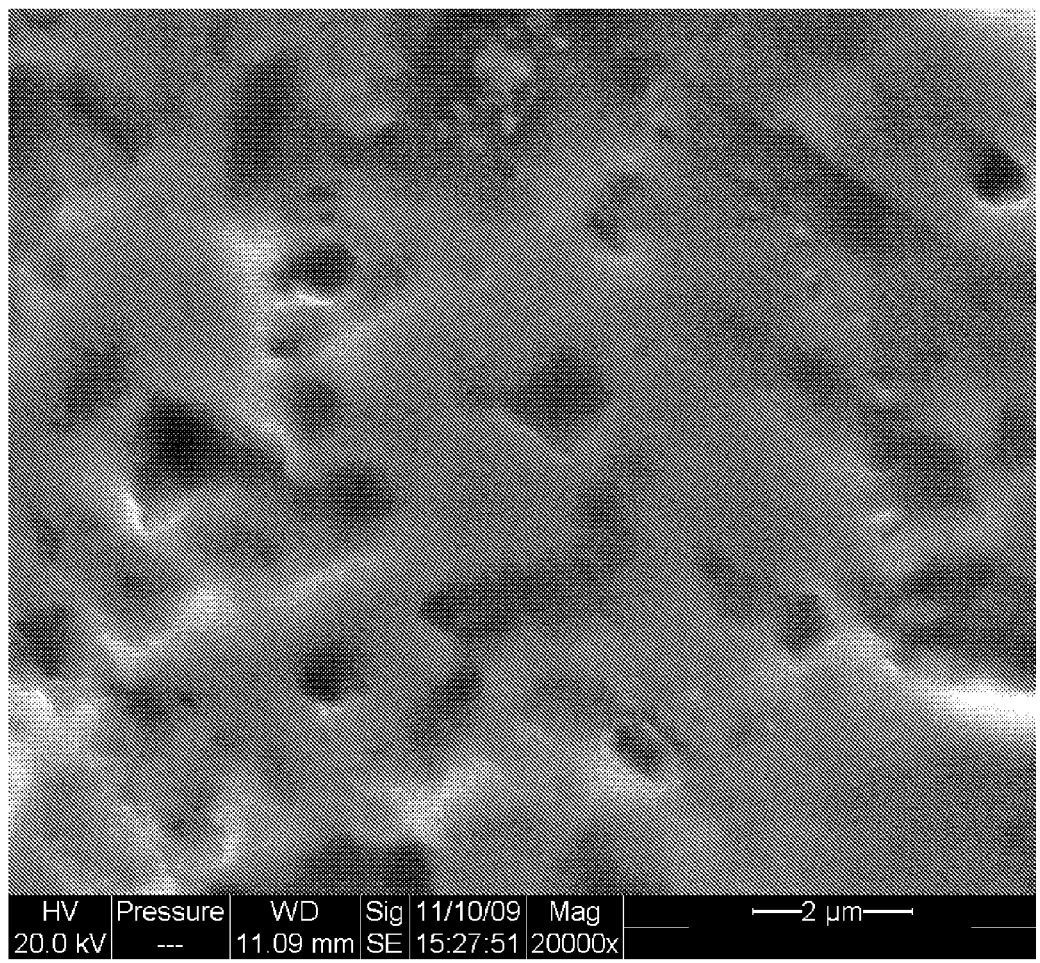
FIG. 3A presents a secondary electron micrograph showing a Zr-blast (zirconium dioxide particle) surface of a cast cobalt-chromium-molybdenum alloy substrate having a smooth surface with scattered indentations of a couple of microns used for a tensile adhesion test, implementing a portion of embodiments of the present invention.
Figure 3B:
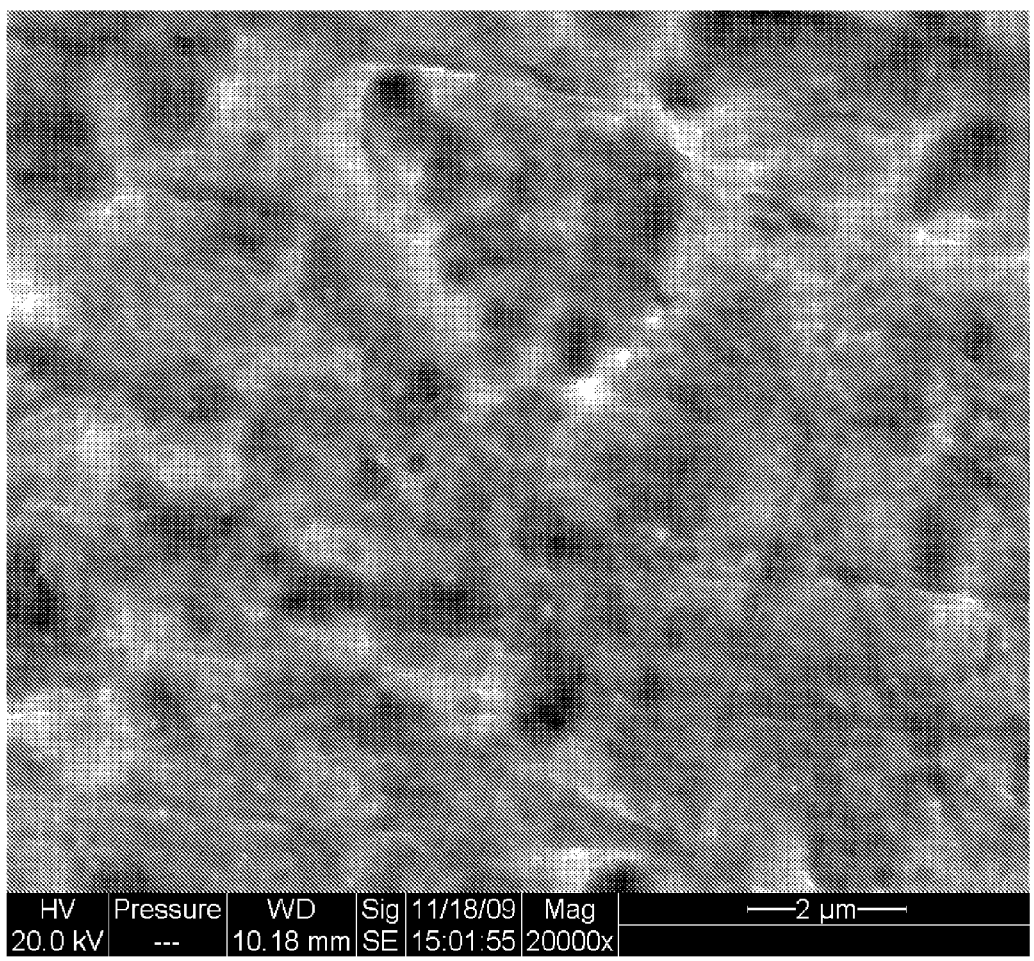
FIG. 3B presents a secondary electron micrograph of a surface prepared as described in the caption for FIG. 3A that is subsequently treated with a hydrochloric acid solution, the surface has interconnected etched pits of a couple of hundred nanometers covering the entire surface and scattered indentation of a couple of microns.

Representative secondary electron micrographs (Quanta 600F operating in high vacuum at 20 KV, spot size 3, and work distance of 6-15 mm) of a control sample surface and a treated sample surface are presented in FIGS. 3A and 3B, respectively.

The $R_a$ of a number of the control samples and treated samples were measured using a contact profilometer (Zeiss Surfcom 5000) utilizing a standard diamond stylus having a tip size of 1.5-2.0 microns. Four measurements were collected at 0°, 90°, 180°, 270° along the radial direction of the flat surface for each sample. The sample length was 0.8 mm and evaluation length was 0.8 mm×5 (i.e., five sample lengths of 0.8 mm were used to evaluate a given $R_a$ value). Six samples of each sample type were measured to determine an average $R_a$ value for the samples.

The tensile strength of a cement bond formed with the control samples (n=10) and the treated samples (n=10) was determined using the following protocol. DePuy SmartSet® MV cement was molded to each specimen in the fluid-form, having a cured-volume of 28.5-mm$^3$ and allowed to cure at ambient air for a minimum of 24-hours. The specimen was then inserted into pinned clevis fixtures attached to a MTS Alliance RF/100 static test frame where a static tensile load was applied to the specimen at 2.54-mm/minute until fracture. Each sample contained 5 specimens.

TABLE 1

Results of Testing Zirconia Blasted Samples

|  | Control Samples | Treated Samples |
| --- | --- | --- |
| $R_a$ (μm) | 0.66 ± 0.15 | 0.65 ± 0.13 |
| Tensile Strength (MPa) | 2.5 ± 1.3 | 6.9 ± 2.1 |

The results of the $R_a$ and tensile strength measurements are summarized in Table 1. In general, the treatment with the acid does not statistically affect the average $R_a$ value of the sample. However, the tensile strength of a cement bond formed with the treated sample shows a surprising increase of over 275%.

Example 2

Comparison of Shear Strength of Control and Treated Surfaces

Samples were formed from casted CoCrMo (ASTM F75) shear pins having a size of 0.25" (diameter)×4" (length). The surface roughness of these pins originated from roughness associated with cast molding and subsequent surface scale cleaning.

A number of these samples were reserved for testing; these were designated as control samples. The remaining samples were further treated with a hydrochloric acid solution exhibiting a concentration of 8N at a room condition of 18-23° C. for a period of 24 hours. The parts were subsequently rinsed in RO water, ultrasonically cleaned in RO water for 20 minutes, then ultrasonically cleaned in RO water for 10 minutes and 5 minutes with interstitial rinsings in RO water. The cylinders are then dried at 60° C. for at least 2 hours in an oven The acid treated samples were designated as treated samples.

Figure 4A:
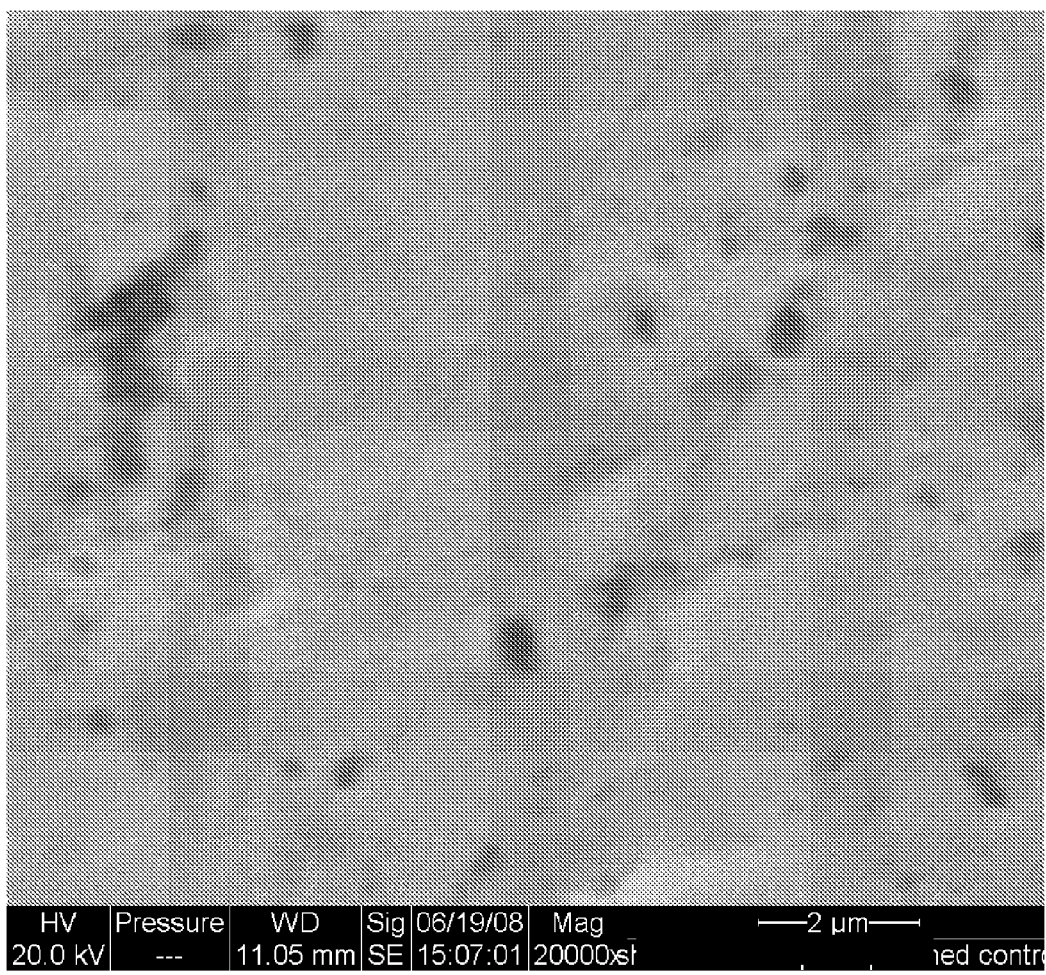
FIG. 4A presents a backscattered electron image of a control sample of a casted CoCrMo shear pin (0.25" diameter and 4" long) to be used in a ring shear adhesion test, the shear pin surface has a smooth area with occasional surface defects/indentations at the micron size scale.
Figure 4B:
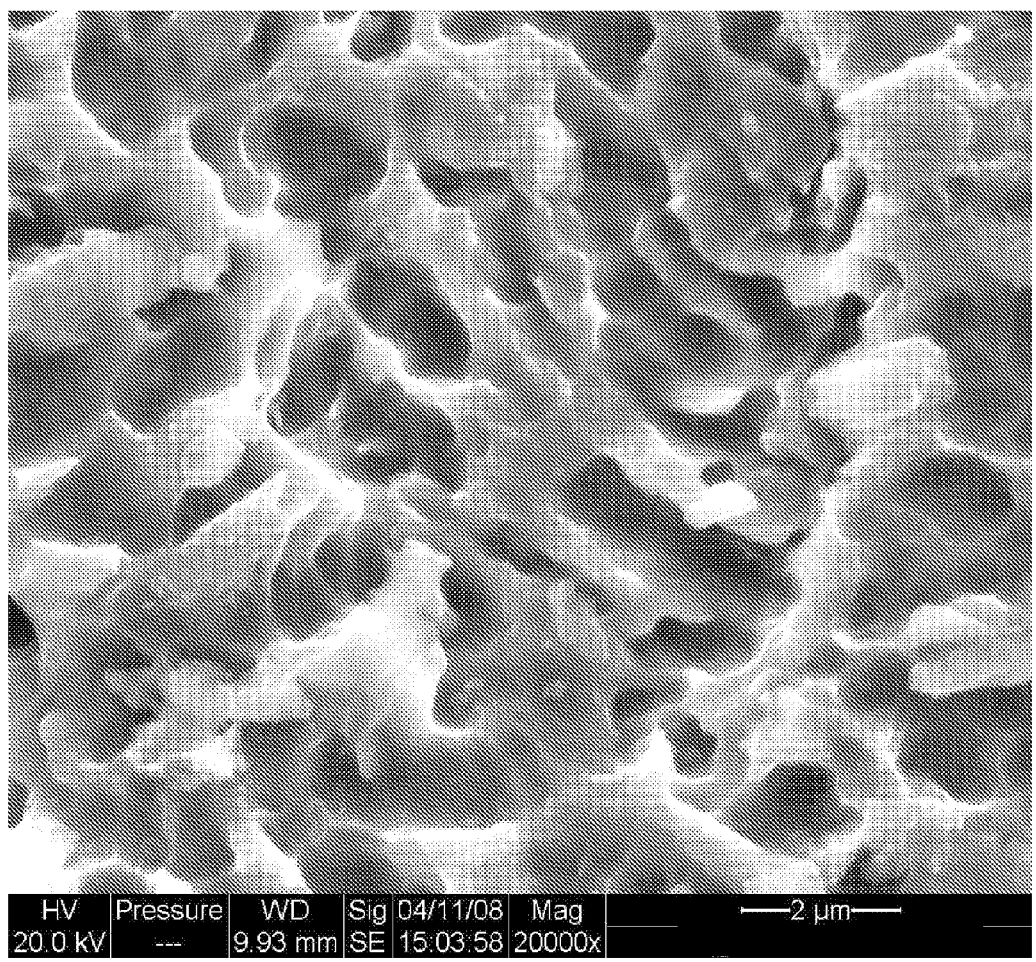
FIG. 4B presents a backscattered electron image of a surface initially prepared as described in caption for FIG. 4A and subsequently treated with a hydrochloric acid solution, the surface of the treated shear pin shows interconnected acid etched pits of one to several microns.

Representative secondary electron micrographs, using a backscattered electron detector (Quanta 600F operating in high vacuum at 20 KV, spot size 3, and work distance of 8-15 mm) of a control sample surface and a treated sample surface are presented in FIGS. 4A and 4B, respectively.

The $R_a$ of a number of the control samples and treated samples were measured using a contact profilometer (Zeiss Surfcom 5000 utilizing a standard diamond stylus having a tip size of 1.5-2.0 microns. Four measurements were collected on the surface following long-axis at a rotation of 0°, 90°, 180°, 270° for each sample. The sample length was 0.8 mm and the evaluation length was 0.8 mm×5 (i.e., five sample lengths of 0.8 mm were used to evaluate a given $R_a$ value). Ten samples of each sample type (control and treated) were measured to determine an average $R_a$ value for the samples.

The results of the $R_a$ measurements indicate that the control samples exhibit an average $R_a$ value of 0.40 μm±0.06 μm, and the treated samples exhibit an average $R_a$ value of 0.38 μm±0.05 μm. Accordingly, the treatment samples have statistically the same $R_a$ as the control samples.

Figure 5:
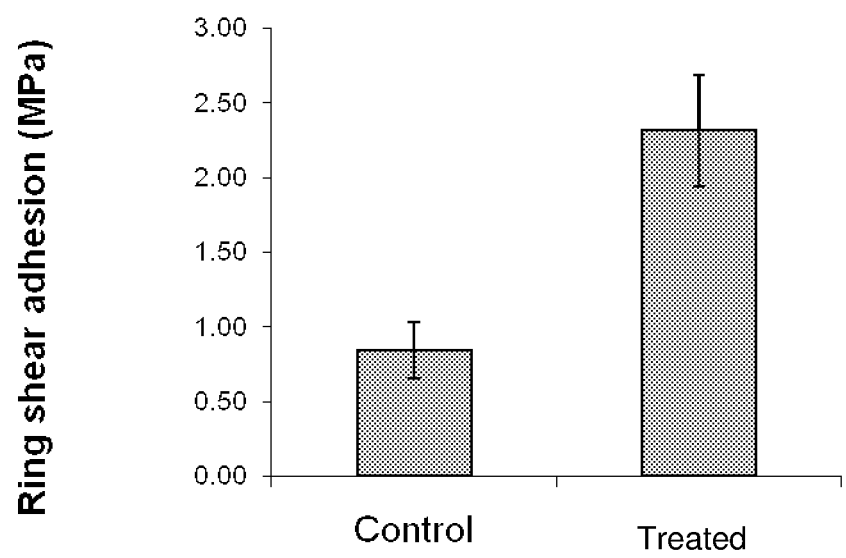
FIG. 5 presents a bar graph depicting the ring shear adhesion strengths of the control and treated samples depicted in FIGS. 4A and 4B, the height of the wide bars indicate the average shear strength of the corresponding type of sample, and the position of the thin bars corresponding with the distribution of values of the individual samples.
Figure 6A:
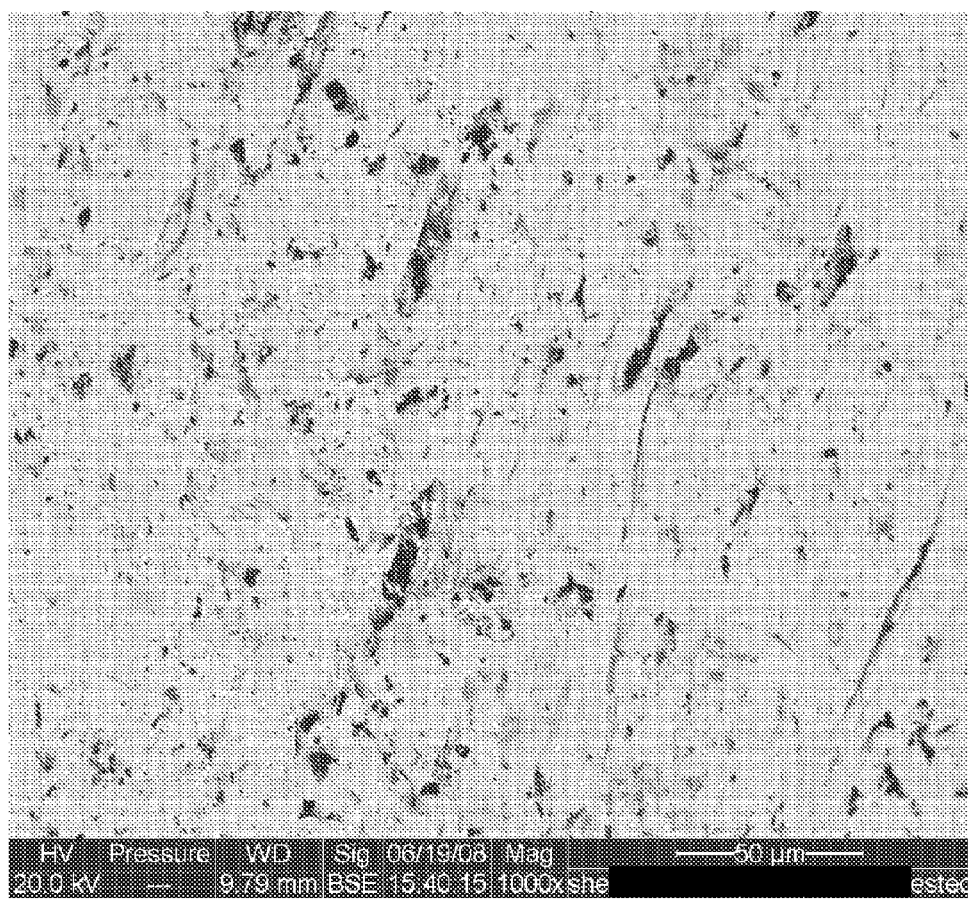
FIG. 6A presents a backscattered electron image of the surface of the control sample after the ring-shear experiment.
Figure 6B:
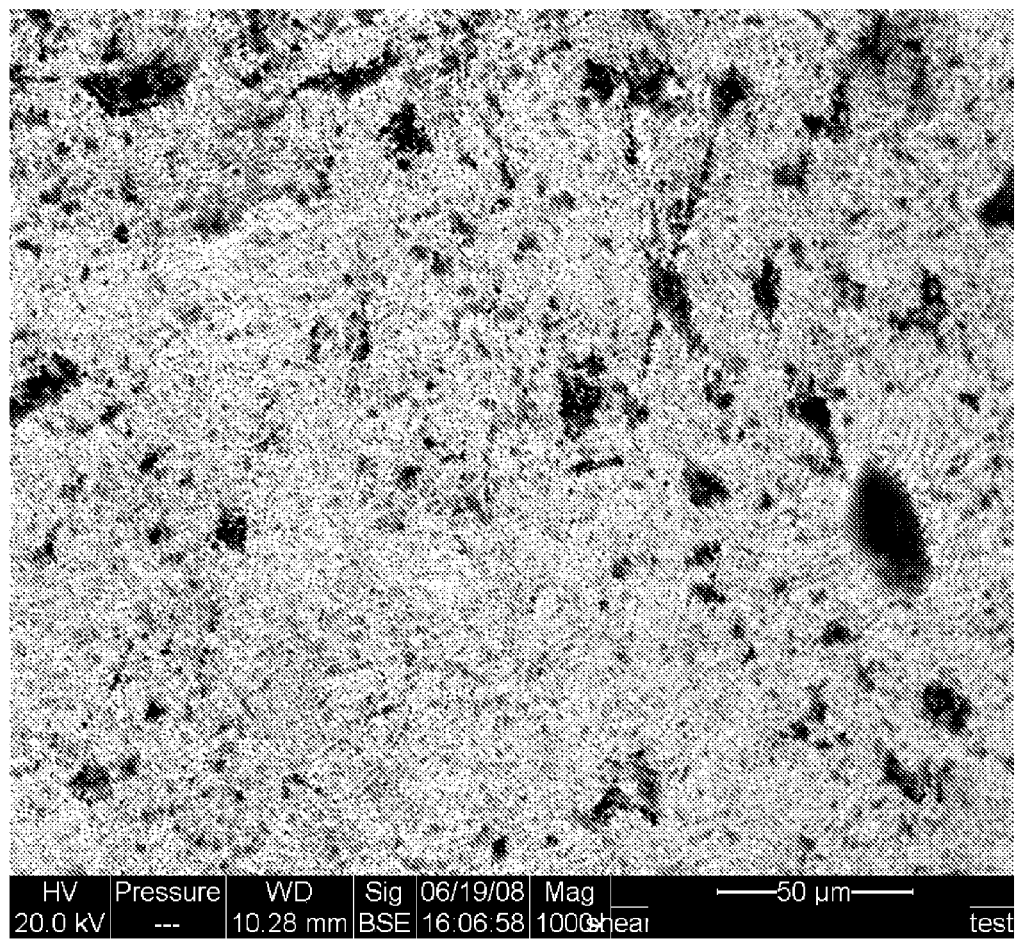
FIG. 6B presents a backscattered electron image of a treated sample after a ring-shear experiment, the darker particles indicate the increased presence of PMMA cement attached onto the treated surfaces vis-à-vis the control sample depicted in FIG. 6A due to better mechanical interlocking at interface of treated sample/PMMA cement than control.

Ten control samples and ten treated samples were tested in a ring shear pull out study. The results of the ring shear adhesion measurements are presented in FIG. 5 with the height of the bars indicating the average ring shear stress, and the error bars indicating the range of values measured for each of the sample types. Representative backscattered electron micrographs (Quanta 600F operating in high vacuum at 20 KV, spot size 3, and work distance of 8-15 mm) of the control and treated surfaces after testing are provided in FIGS. 6A and 6B, respectively. The residue of the polymethyl methacrylate cement appears as dark spots on the images in FIGS. 6A and 6B. The larger number of residues on the treated surface indicate generally greater adhesion of the cement with the substrate surface.

Example 3

Alumina/Glass Blasted Substrates—Control and Treated Samples

Cast cobalt-chromium-molybdenum (ASTM F75) rod stock (0.75" diameter and several feet long) are machine cut to 0.75" (diameter)×1.5" (length) cylinders. The test surface was buffed ($R_a$<0.2 micron) before zirconia blasting to remove artifacts of machining. The test cylinders were particle blasted ("P-blasted") with a 50/50 mixture of 60 grit alumina particles/60 grit glass beads at typical room conditions using a work distance of about 4 to 8 inches at 20 PSI for a blasting time of about 5 to about 30 seconds. The blasted surfaces were blown clean with compressed air followed by ultrasonic cleaning in detergent (1-2% Alconox) and reverse osmosis ("RO") water. The surfaces were then dried at 60° C.

A number of these samples were reserved for testing; these were designated as control samples. The remaining samples were further treated with a hydrochloric acid solution exhibiting a concentration of 8N at a room condition of 18-23° C. for a period of 24 hours. The parts were subsequently rinsed in RO water, ultrasonically cleaned in RO water for 20 minutes, then ultrasonically cleaned in RO water for 10 minutes and 5 minutes with interstitial rinsings in RO water. The cylinders are then dried at 60° C. for at least 2 hours in an oven The acid treated samples were designated as treated samples.

Figure 7A:
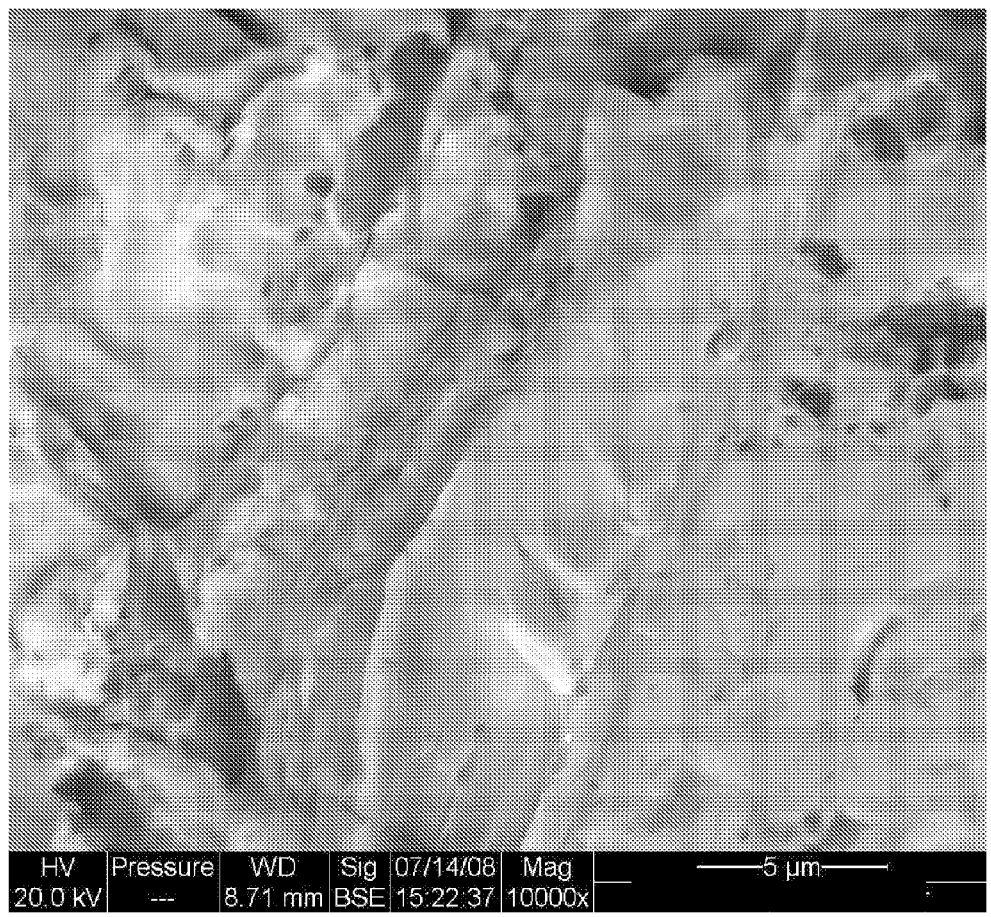
FIG. 7A presents a backscattered electron micrograph of a cobalt-chromium-molybdenum alloy substrate surface blasted with a P-blast (50/50 mixture of 60 grit aluminum oxide particles and glass beads), showing an irregular deformed surface pattern and implementing a portion of embodiments of the present invention.
Figure 7B:
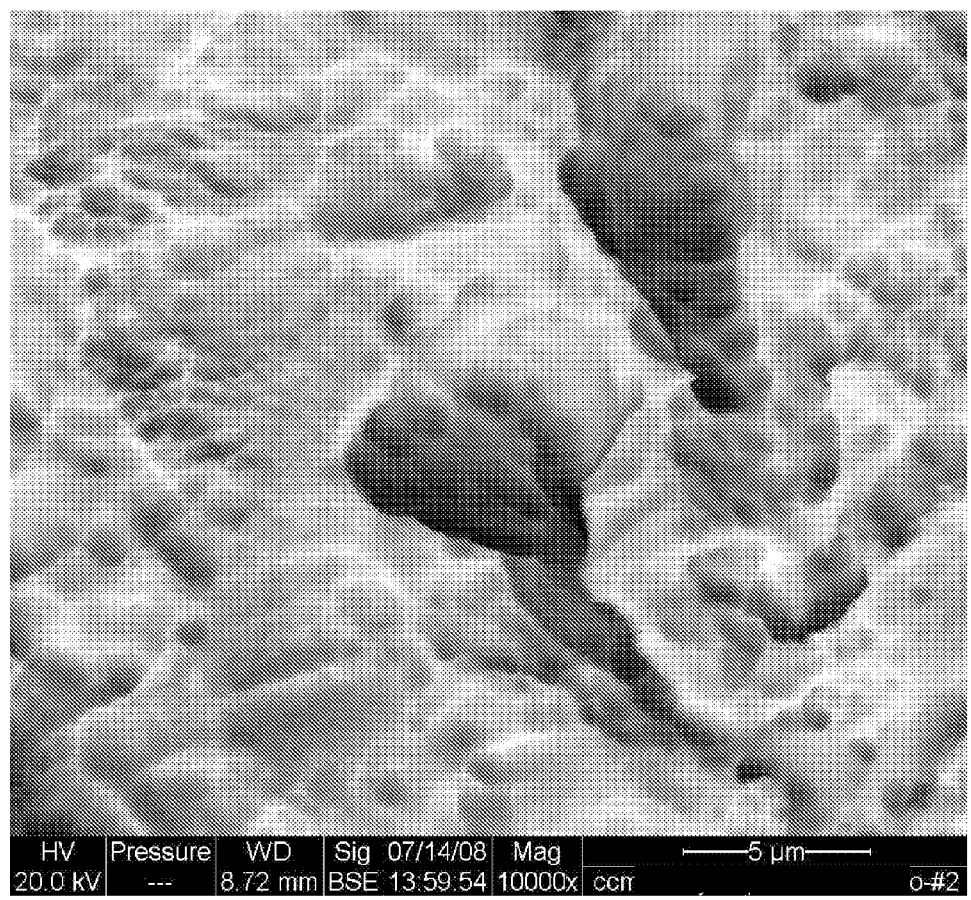
FIG. 7B presents a backscattered electron micrograph of a surface prepared as described in the caption for FIG. 7A that is subsequently treated with a hydrochloric acid solution, the surface shows continuous micron and submicron round etched pits/indentations.

Representative backscattered electron micrographs (Quanta 600F operating in high vacuum at 20 KV, spot size 3, and work distance of 8-15 mm) of a control sample surface and a treated sample surface are presented in FIGS. 7A and 7B, respectively. FIG. 7A provides indications of interstitial grit (dark spots) embedded in the sample surface. FIG. 7B shows that a substantial number of the embedded grit particles have been removed from the surface> As well, the treated sample surface exhibits round surface pits, presumably formed during surface etching by the treatment formulation.

The $R_a$ of a number of the control samples and treated samples were measured using a contact profilometer (Zeiss Surfcom 5000) utilizing a standard diamond stylus having a tip size of 1.5-2.0 microns. Four measurements were collected at 0°, 90°, 180°, 270° along the radial direction of the flat surface for each sample. The sample length was 0.8 mm and the evaluation length was 0.8 mm×5 (i.e., five sample lengths of 0.8 mm were used to evaluate a given $R_a$ value). Three samples of each sample type were measured to determine an average $R_a$ value for the samples.

The tensile strength of a cement bond formed with the control samples (n=4) and the treated samples (n=4) was determined using the following protocol. DePuy SmartSet® MV cement was molded to each specimen in the fluid-form, having a cured-volume of 28.5-mm³ and allowed to cure at ambient air for a minimum of 24-hours. The specimen was then inserted into pinned clevis fixtures attached to a MTS Alliance RF/100 static test frame where a static tensile load was applied to the specimen at 2.54-mm/minute until fracture.

TABLE 2

Results of Testing Alumina/Glass Blasted Samples

| | Control Samples | Treated Samples |
|---|---|---|
| $R_a$ (μm) | 1.58 ± 0.07 | 1.58 ± 0.11 |
| Tensile Strength (MPa) | 16.7 ± 1.0 | 22.7 ± 1.9 |

The results of the $R_a$ and tensile strength measurements are summarized in Table 2. In general, the treatment with the acid does not statistically affect the average $R_a$ value of the sample. However, the tensile strength of a cement bond formed with the treated sample shows an increase of almost 36%.

The tensile fatigue strength of a cement bond formed with the control samples and the treated samples was determined using the following protocol. DePuy SmartSet® MV was molded to each specimen in the fluid-form, having a cured-volume of 28.5-mm³ and allowed to cure at ambient air for a minimum of 24 hours. The specimen was then inserted into pinned clevis fixtures attached to a MTS servo-hydraulic test frame where a cyclic tensile load was applied at the specified stress-level at 2-Hz until fracture or until runout (i.e., a condition where a sample does not fail after being subject to a predetermined number of cycles). A displacement limit of +2.54-mm was used to indicate failure. To determine the fatigue strength of each sample, 8-specimens each were needed to produce 2-runnouts at the maximum fatigue stress.

Figure 8:
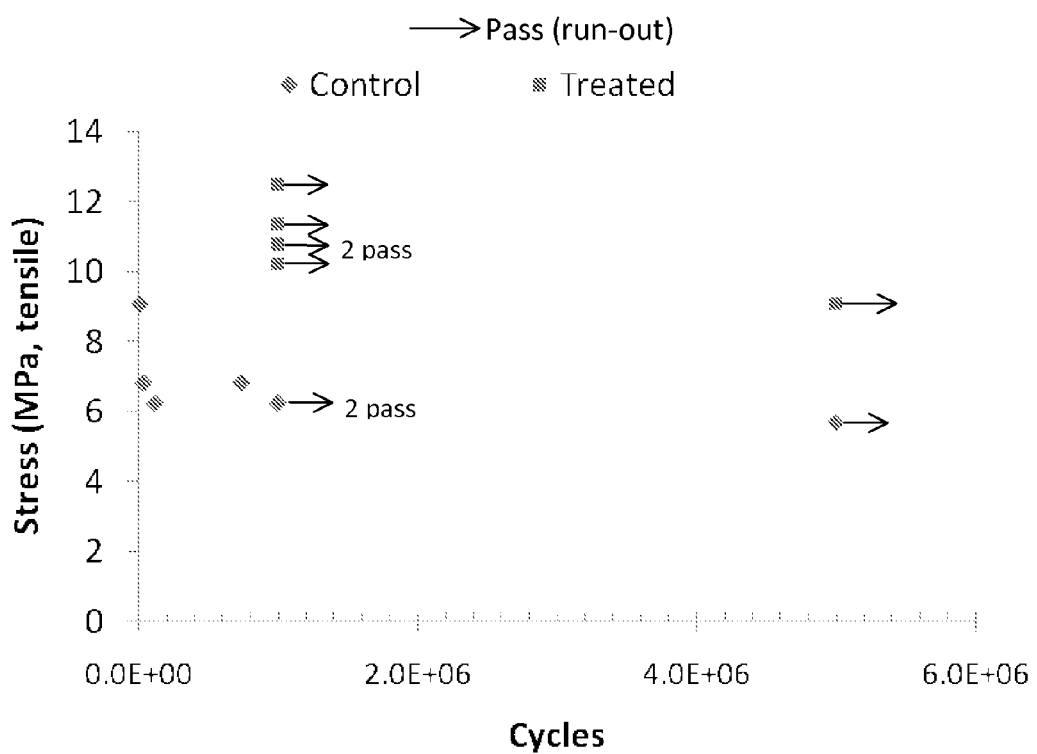
FIG. 8 presents a graph depicting the results of tensile strength fatigue tests of the alumina/glass blasted substrates described in the captions for FIGS. 7A and 7B, the arrows indicating that a runout condition was achieved without failure after a selected number of testing cycles.

A graph depicting the results of the fatigue testing is shown in FIG. 8. The presence of an arrow originating from a data point indicates that a runout condition, and the indicator "2 pass" indicates that two separate samples achieved the same runout condition. In general, the results indicate that treated samples require a substantially higher tensile load and/or more cycles before fracturing occurs.

Example 4

Comparison of $R_a$, $R_q$, $R_z$, and $R_{sk}$ Values in Alumina/Glass Grit Blasted Samples Four treated and four control samples were prepared in accord with the tensile fatigue test procedures described in Example 3 above. $R_a$, $R_q$, $R_z$, and $R_{sk}$ values were determined for each of the samples. The roughness values were all determined using a contact profilometer (Zeiss Surfcom 5000) utilizing a standard diamond stylus having a tip size of 1.5-2.0 microns. Four measurements were collected at 0°, 90°, 180°, 270° along the radial direction of the flat surface for each sample, and associated $R_a$, $R_q$, $R_z$, and $R_{sk}$ values were calculated. The sample length was 0.8 mm and evaluation length was 0.8 mm×5 (i.e., five sample lengths of 0.8 mm were used to evaluate a given $R_a$ value). Four samples of each sample type were each measured to determine an average $R_a$, $R_q$, $R_z$, and $R_{sk}$ value for the samples. The averaged results are summarized in Table 3.

TABLE 3

Averaged Measured Values of Roughness for Samples

|  | Control | Treated |
|---|---|---|
| $R_a$ (μm) | 1.46 ± 0.07 | 1.56 ± 0.10 |
| $R_q$ (μm) | 1.92 ± 0.11 | 2.02 ± 0.10 |
| $R_z$ (μm) | 11.72 ± 0.96 | 11.67 ± 0.40 |
| $R_{sk}$ (μm) | −0.30 ± 0.07 | −0.66 ± 0.10 |

The results of the measured $R_a$, $R_q$, $R_z$, and $R_{sk}$ values for the control and treated samples are shown in Table 3. In general, the difference in average values for $R_a$, $R_q$, and $R_z$ between the control and treated samples are not statistically different. The $R_{sk}$ value of the treated samples is more negative than the $R_{sq}$ value for the control samples, indicating that the treated sample surface exhibits negative draft and a less abrasive surface.

Example 5

Comparison of $R_a$ and $R_{sk}$ Values for Zr and P Blasted Surfaces

Twelve cast CoCrMo (F75) disks (0.75" diameter and 0.125" thick) were prepared and either Zr-blasted (n=6) in accord with the description of Example 1, or P-blasted (n=6) in accord with the description of Example 3. Blasted surfaces were blown clean with compressed air followed by ultrasonic cleaning in detergent (1-2% Alconox) and reverse osmosis ("RO") water. The surfaces were then dried at 60° C. Surface roughness values for $R_a$ and $R_{sk}$ were measured for all twelve disks using a contact profilometer (Zeiss Surfcom 5000) utilizing a standard diamond stylus having a tip size of 1.5-2.0 microns. Four measurements were collected at 0°, 90°, 180°, 270° along the radial direction of the flat surface for each sample. The sample length was 0.8 mm and the evaluation length was 0.8 mm×5 (i.e., five sample lengths of 0.8 mm were used to evaluate a given $R_a$ value). The average and the standard deviation of the $R_a$ and $R_{sk}$ values was calculated for the Zr-blasted and P-blasted samples.

Next, all disks were acid treated in 8N HCl at room conditions (18-23° C.) for 24 hours. were subsequently rinsed in RO water, ultrasonically cleaned in RO water for 20 minutes, then ultrasonically cleaned in RO water for 10 minutes and 5 minutes with interstitial rinsings in RO water. The cylinders are then dried at 60° C. for at least 2 hours in an oven The acid treated samples were designated as treated samples. $R_a$ and $R_{sk}$ values of the disks were measured using the contact profilometer after acid treatment. The average and the standard deviation of the $R_a$ and $R_{sk}$ values of the treated samples was calculated.

TABLE 4

Summary of $R_a$ and $R_{sk}$ Mean Values and Standard Deviations

|  | $R_a$ (μm) | | $R_{sk}$ (μm) | |
|---|---|---|---|---|
|  | blast only | acid treated | blast only | acid treated |
| Zr-blasted | 0.580 ± 0.136 | 0.573 ± 0.094 | −0.216 ± 0.301 | −0.642 ± 0.176 |
| P-blasted | 0.997 ± 0.037 | 1.054 ± 0.048 | −0.249 ± 0.334 | −0.574 ± 0.142 |

Table 4 above lists the mean and standard deviation of $R_a$ and $R_{sk}$ values. Variable analysis was conducted using two-way ANOVA employing Minitab software (Minitab® 15.1.1.0). Two-way ANOVA analysis showed that acid treatment did not statistically change surface roughness $R_a$ (p=0.501) while acid treatment did significantly change $R_{sk}$ (p=0.002).

Example 6

Testing of Control and Treated Knee Implants

Femoral knee implants (Sigma Knee Implant, DePuy Orthopaedics) were tested in accord with the following procedures. The implants were casted and grit-blasted. The blasted surfaces were blown clean with compressed air followed by ultrasonic cleaning in detergent (1-2% Alconox) and reverse osmosis ("RO") water. The surfaces were then dried at 60° C. Some of the implants, designated control, were not further treated. The remaining implant samples, designated treated samples, were exposed to 8N HCl at room conditions (18-23° C.) for 24 hours. The treated implants were subsequently rinsed in RO water, ultrasonically cleaned in RO water for 20 minutes, then ultrasonically cleaned in RO water for 10 minutes and 5 minutes with interstitial rinsings in RO water. The cylinders are then dried at 60° C. for at least 2 hours in an oven The acid treated samples were designated as treated samples.

Figure 9A:
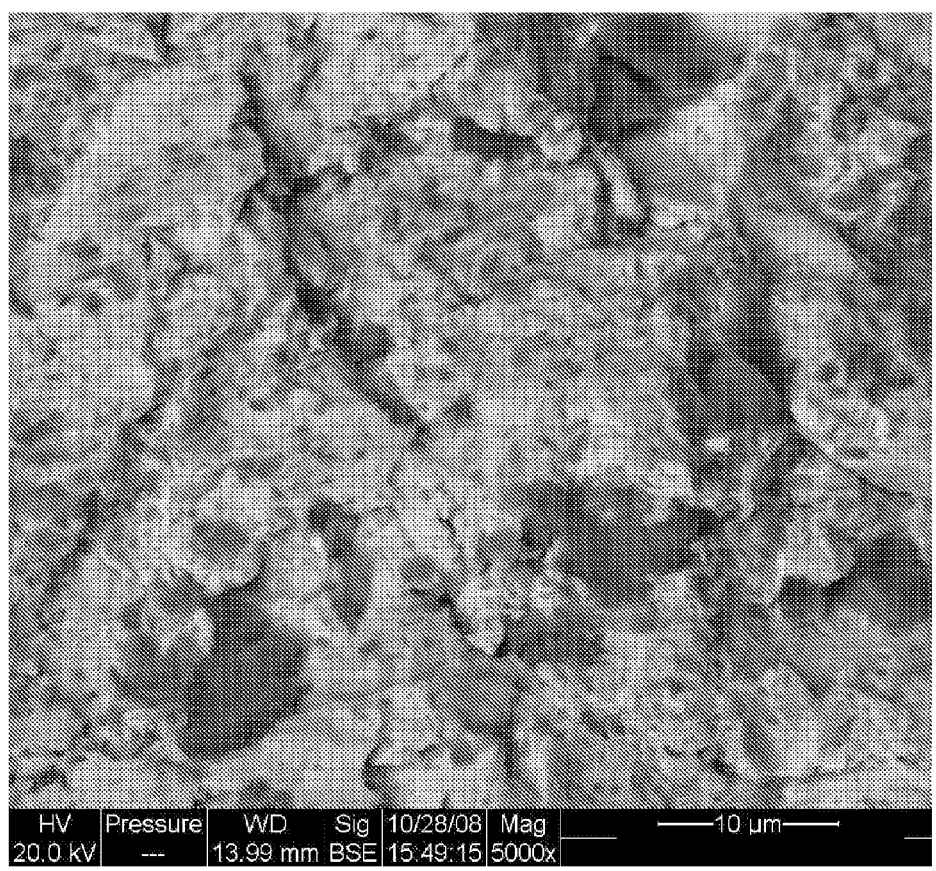
FIG. 9A presents a backscattered electron micrograph of a cobalt-chromium-molybdenum alloy femoral knee implant surface for contacting with PMMA cement, the alumina blasted surface shows an irregular deformed surface pattern with grit-blasting residues (dark spots), implementing a portion of embodiments of the present invention.
Figure 9B:
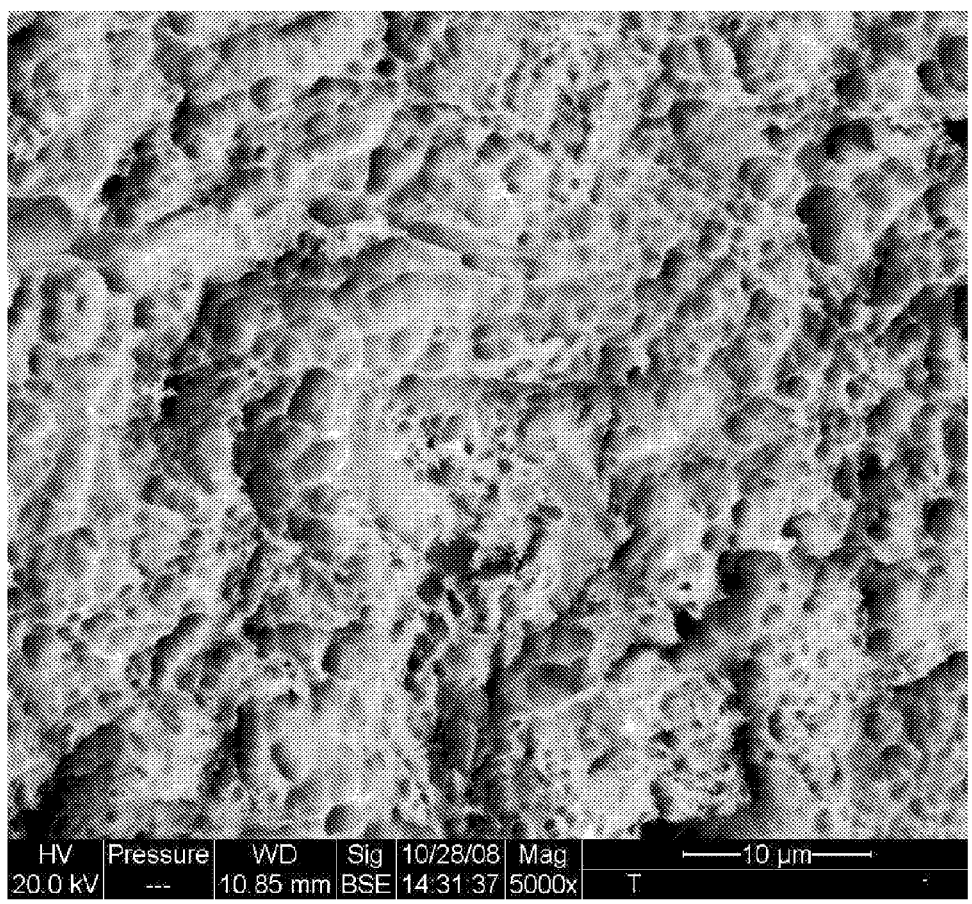
FIG. 9B presents a backscattered electron micrograph of an implant surface initially prepared as described in the caption for FIG. 9A and subsequently treated with a hydrochloric acid solution; the surface shows continuous micron and submicron round etched pits/indentations.

FIG. 9A provides a backscattered electron micrograph (Quanta 600F operating in high vacuum at 20 KV, spot size 3, and work distance of 8-15 mm) of a control implant surface. The dark spots in the micrograph provide indications of interstitial grit embedded in the sample surface. FIG. 9B provides a backscattered electron micrograph of a treated implant surface. As can be seen, a substantial number of the embedded grit particles have been removed from the surface, and round surface pits have been formed after treatment.

The amount of grit blast residue in the control and treated sample surfaces was determined using energy dispersive x-ray spectroscopy ("EDS") using an instrument from Oxford Industries. The EDS was performed at 20 KV, spot size 4, work distance 11-12 mm at high vacuum. Three random sites of interest (each area=1.36 mm×1.36 mm) were chosen per sample surface to collect data and calculate atomic amount of the grit metallic element (aluminum) normalized by the base alloy atomic concentration (Co, Cr and Mo). The surface coverage of grit residue=Al % atm/sum(Co % atm, Cr % atm, Mo % atm), where % atm is atomic percentage.

Figure 10:
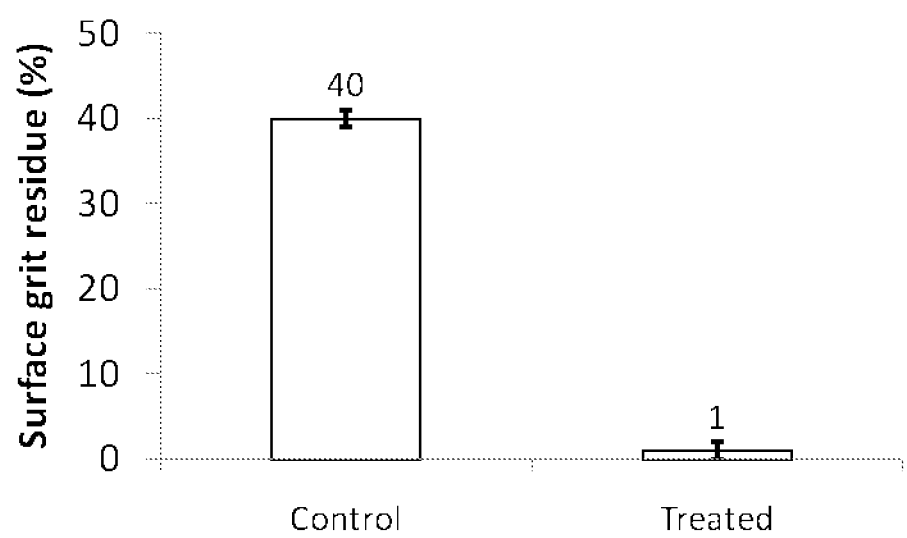
FIG. 10 presents a bar graph depicting the areal surface grit residue as determined by x-ray photoelectron spectroscopy of the control and treated samples depicted in FIGS. 9A and 9B, the height of the wide bars indicate the average surface grit reside percentage of the corresponding type of sample, and the position of the thin bars corresponding with the distribution of values of the individual samples.

The results of the testing are shown in the bar graph of FIG. 10 indicate that the control sample is approximately 40% covered by grit, while the treated sample is approximately 1% covered by grit.

EQUIVALENTS

While the present invention has been described in terms of specific methods, structures, and devices it is understood that variations and modifications will occur to those skilled in the art upon consideration of the present invention. For example, the methods and compositions discussed herein can be utilized beyond the preparation of metallic surfaces for implants in some embodiments. As well, the features illustrated or described in connection with one embodiment can be combined with the features of other embodiments. Such modifications and variations are intended to be included within the scope of the present invention. Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims.

All publications and references are herein expressly incorporated by reference in their entirety. The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method for preparing a biomedical implant comprising:
    preparing an implant having a first roughened surface exhibiting a first $R_a$ value in a range of about 0.1 microns to about 100 microns; and
    exposing the first roughened surface of the implant to a treatment formulation comprising a hydrohalic acid to form a second roughened surface exhibiting a second $R_a$ value that is substantially similar to the first $R_a$ value, the second roughened surface also having a lower $R_{sk}$ value than an $R_{sk}$ value of the first roughened surface;
    wherein the tensile strength of a bond between cement and the second roughened surface is at least about 30% higher than the strength of a bond between cement and the first roughened surface; and
    wherein the second $R_a$ value differs from the first $R_a$ value by less than about 20%.

2. The method of claim 1, wherein preparing the implant having the first roughened surface comprises roughening a substrate surface using at least one of blasting, grinding, spraying, cast molding, and mechanical deformation.

3. The method of claim 2, wherein preparing the implant having the first roughened surface comprises particle blasting the implant to form the first roughened surface.

4. The method of claim 3, wherein particle blasting comprises using particles comprising at least one of an inorganic material and glass.

5. The method of claim 3, wherein particle blasting comprises embedding at least one particle in the first roughened surface, and exposing the first roughened surface to the treatment formulation comprises removing the at least one particle from the first roughened surface.

6. The method of claim 3, wherein the second roughened surface is substantially free of particles from particle blasting.

7. The method of claim 3, wherein the second roughened surface exhibits a surface coverage of non-native material from particle blasting of less than about 30% as measured by energy dispersive x-ray spectroscopy.

8. The method of claim 1, wherein exposing the first roughened surface comprises treating the first roughened surface with an acid formulation.

9. The method of claim 1, wherein the implant formed by the method exhibits at least one of improved tensile strength, improved shear strength, and improved tensile fatigue strength of a cement bond when the cement bond is formed between cement and the second roughened surface of the implant relative to a cement bond formed between cement and the first roughened surface of the implant.

10. The method of claim 1, wherein the cement comprises polymethyl methacrylate (PMMA).

11. The method of claim 1, wherein the treatment formulation substantially excludes hydrogen fluoride and fluoride salts.

* * * * *